(12) United States Patent
Goda

(10) Patent No.: US 10,314,324 B2
(45) Date of Patent: Jun. 11, 2019

(54) METHOD FOR PRODUCING CHLOROUS ACID AQUEOUS SOLUTION BY ADSORPTION OF CHLORINE DIOXIDE

(71) Applicant: HONBU SANKEI CO., LTD., Osaka (JP)

(72) Inventor: Hisataka Goda, Osaka (JP)

(73) Assignee: HONBU SANKEI CO., LTD., Osaka (JP)

( * ) Notice: Subject to any disclaimer, the term of this patent is extended or adjusted under 35 U.S.C. 154(b) by 0 days.

(21) Appl. No.: 15/105,185

(22) PCT Filed: Dec. 22, 2014

(86) PCT No.: PCT/JP2014/006379
§ 371 (c)(1),
(2) Date: Jun. 16, 2016

(87) PCT Pub. No.: WO2015/093062
PCT Pub. Date: Jun. 25, 2015

(65) Prior Publication Data
US 2016/0338391 A1 Nov. 24, 2016

(30) Foreign Application Priority Data

Dec. 20, 2013 (JP) ................................. 2013-263945

(51) Int. Cl.
*A01N 25/02* (2006.01)
*A01N 59/00* (2006.01)
(Continued)

(52) U.S. Cl.
CPC .............. *A23L 3/358* (2013.01); *A01N 59/00* (2013.01); *C01B 11/08* (2013.01); *A23V 2002/00* (2013.01)

(58) Field of Classification Search
CPC ........... A23L 3/34; A23L 3/3454; A23L 3/358; A01N 59/00; A01N 59/26; A01N 59/08; A01N 25/22; C01B 11/08
See application file for complete search history.

(56) References Cited

U.S. PATENT DOCUMENTS

| 3,123,521 A | * | 3/1964 | Wentworth et al. | .... A23L 3/358 210/754 |
| 3,585,147 A | * | 6/1971 | Gordon et al. | ........... C02F 1/76 252/187.21 |

(Continued)

FOREIGN PATENT DOCUMENTS

| CN | 103101883 A | 5/2013 |
| CN | 103314996 A | 9/2013 |

(Continued)

OTHER PUBLICATIONS

International Search Report for corresponding International Application No. PCT/JP2014/006379 dated Mar. 10, 2015.
(Continued)

*Primary Examiner* — Lakshmi S Channavajjala
(74) *Attorney, Agent, or Firm* — Renner, Otto, Boisselle & Sklar, LLP

(57) ABSTRACT

The present invention addresses the problem of providing a novel technique for producing aqueous chlorous acid. The present invention provides a method for producing chlorous acid, which comprises a step of adding chlorine dioxide ($ClO_2$) to one or more components independently selected from an inorganic acid, an inorganic acid salt, an organic acid and an organic acid salt or a combination of two or more of the aforementioned components. In the method, chlorine dioxide ($ClO_2$) is provided in the form of a gas. The method also comprises, subsequent to the above-mentioned addition step, a step of further adding one or more components independently selected from an inorganic acid, an inorganic
(Continued)

acid salt, an organic acid and an organic acid salt or a combination of two or more of the aforementioned components.

15 Claims, 8 Drawing Sheets

(51) Int. Cl.
*A01N 59/08* (2006.01)
*C01B 11/08* (2006.01)
*A23L 3/358* (2006.01)

(56) References Cited

U.S. PATENT DOCUMENTS

| | | | |
|---|---|---|---|
| 6,200,557 | B1 | 3/2001 | Ratcliff |
| 8,951,576 | B2 * | 2/2015 | Goda .................. A01N 59/00 424/405 |
| 9,516,878 | B2 * | 12/2016 | Goda .................. A01N 59/00 |
| 9,521,841 | B2 * | 12/2016 | Goda .................. A01N 59/00 |
| 2010/0003342 | A1 | 1/2010 | Ito |
| 2010/0330202 | A1 | 12/2010 | Goda |

FOREIGN PATENT DOCUMENTS

| | | |
|---|---|---|
| EP | 0482811 A1 | 4/1992 |
| EP | 2130542 A1 | 12/2009 |
| JP | 51-82080 A | 7/1976 |
| JP | 56-92102 A | 7/1981 |
| JP | 2010-77004 A | 4/2010 |
| JP | 2013-100346 A | 5/2013 |
| WO | WO 2008/026607 A1 | 3/2008 |
| WO | WO 2008/072388 A1 | 6/2008 |

OTHER PUBLICATIONS

International Preliminary Report on Patentability for corresponding International Application No. PCT/JP2014/006379 dated Jul. 14, 2015.
Translation of International Preliminary Report on Patentability for corresponding International Application No. PCT/JP2014/006379 dated Jun. 23, 2016.
Official Action for related Chinese Application No. 201480068694.0 dated Feb. 27, 2017 and its English translation.
First Examiner's Report for related Australian Application No. 2014368266 dated Oct. 21, 2016.
Extended European search report for related European Application No. 14872746.4 dated Jul. 24, 2017.
Office Action for related Chinese Application No. 201480068694.0 dated Jan. 10, 2018 and its partial English translation.
Office Action for related Chinese Application No. 201480068694.0 dated Oct. 17, 2018 and its partial English translation.

* cited by examiner

METHOD FOR PRODUCING CHLOROUS ACID AQUEOUS SOLUTION BY ADSORPTION OF CHLORINE DIOXIDE

TECHNICAL FIELD

The present invention relates to a method of manufacturing a chlorous acid aqueous solution by chlorine dioxide adsorption.

BACKGROUND ART

Chlorous acid aqueous solution has drawn attention as a food additive. However, a chlorous acid aqueous solution is problematic in that the manufacture thereof is difficult, and even if the manufacture were possible, the storage in normal condition is not possible.

Meanwhile, the inventors have discovered a method of manufacture of a chlorous acid aqueous solution and have confirmed a sterilizing effect on *E. coli*, which has led to the filing of a patent application (Patent Literature 1).

CITATION LIST

Patent Literature

[PTL 1] International Publication No. WO 2008/026607

SUMMARY OF INVENTION

Solution to Problem

The present invention has discovered, and provides, a technique related to a novel method of manufacturing a chlorous acid aqueous solution.

In one aspect, the present invention provides a method of trapping (capturing or adsorbing) chlorine dioxide gas ($ClO_2$) with one of an inorganic acid, inorganic acid salt, organic acid, and organic acid salt, two or more types thereof or a combination thereof to create a transitional state and delay a decomposition reaction, such that chlorous acid ($HClO_2$) can be stably maintained in water over a long period of time. A preferred embodiment of these methods can utilize a further addition of one of an inorganic acid, inorganic acid salt, organic acid, and organic acid salt, two or more types thereof or a combination thereof to the above-described aqueous solution.

Examples of the above-described inorganic acid include carbonic acid, phosphoric acid, boric acid, and sulfuric acid. Further, examples of inorganic acid salt include carbonate, hydroxide, phosphate, and borate. More specifically, sodium carbonate, potassium carbonate, sodium bicarbonate, potassium bicarbonate or the like may be used as the carbonate; sodium hydroxide, potassium hydroxide, calcium hydroxide, barium hydroxide or the like may be used as the hydroxide; disodium hydrogen phosphate, sodium dihydrogen phosphate, trisodium phosphate, tripotassium phosphate, dipotassium hydrogen phosphate, potassium dihydrogen phosphate or the like may be used as the phosphate; and sodium borate, potassium borate or the like may be used as the borate. Furthermore, examples of the above-described organic acid include succinic acid, citric acid, malic acid, acetic acid, lactic acid and the like. Further, the following are suitable as the organic acid salt: sodium succinate, potassium succinate, sodium citrate, potassium citrate, sodium malate, potassium malate, sodium acetate, potassium acetate, sodium lactate, potassium lactate, calcium lactate and the like.

The present invention also provides the following.

(1) A method of manufacturing a chlorous acid aqueous solution, comprising the step of: adsorbing (trapping) chlorine dioxide ($ClO_2$) to aqueous solution A comprising one of an inorganic acid, inorganic acid salt, organic acid, and organic acid salt, two or more types thereof or a combination thereof.

(2) The method of item 1, further comprising the step of adding the chlorine dioxide in the presence of hydrogen peroxide.

(3) The method of item 1 or 2, wherein a pH of the aqueous solution A is 11.0 or less and 6.0 or greater.

(4) The method of any one of items 1 to 3, wherein a pH of the aqueous solution A is 10.8 or less and 10.2 or greater.

(5) The method of any one of items 1 to 4, wherein TAL of the aqueous solution A is 20 to 2000, wherein the TAL is found by an amount of 0.1N—HCl titration from an initial pH at or below pH of 11.0 to a pH of 4, where the TAL is TAL of the aqueous solution prior to blowing in chlorine dioxide gas, and the aqueous solution prepared after blowing in is a chlorous acid aqueous solution. The aqueous solution at this time has a reduced TAL relative to aqueous solution A. A specific buffering agent (aqueous solution B) as designated in the present invention is added to the aqueous solution to stabilize chlorous acid and chlorite ions. The reason for keeping the initial pH of aqueous solution A low and limiting the range of TAL is to eliminate strong alkaline buffering power unique to sodium hydroxide and to limit an aqueous solution to having buffering power to weakly acidic region to weakly alkaline region.

(6) The method of any one of items 1 to 5, wherein the chlorine dioxide ($ClO_2$) is provided as gas.

(7) The method of any one of items 1 to 6, comprising, after the step of adding, a step of further adding aqueous solution B comprising one of an inorganic acid, inorganic acid salt, organic acid, and organic acid salt, two or more types thereof or a combination thereof.

(8) The method of any one of items 1 to 7, wherein the inorganic acid is carbonic acid, phosphoric acid, boric acid, or sulfuric acid.

(9) The method of any one of items 1 to 8, wherein the inorganic acid salt is carbonate, hydroxide, phosphate, or borate.

(10) The method of item 9, wherein the carbonate is sodium carbonate, potassium carbonate, sodium bicarbonate, or potassium bicarbonate.

(11) The method of item 9, wherein the hydroxide is sodium hydroxide, potassium hydroxide, calcium hydroxide, or barium hydroxide.

(12) The method of item 9, wherein the phosphate is disodium hydrogen phosphate, sodium dihydrogen phosphate, trisodium phosphate, tripotassium phosphate, dipotassium hydrogen phosphate, or potassium dihydrogen phosphate.

(13) The method of item 9, wherein the borate is sodium borate or potassium borate.

(14) The method of any one of items 1 to 13, wherein the organic acid salt is succinic acid, citric acid, malic acid, acetic acid, or lactic acid.

(15) The method of any one of items 1 to 14, wherein the organic acid salt is sodium succinate, potassium succinate, sodium citrate, potassium citrate, sodium malate, potassium malate, sodium acetate, potassium acetate, sodium lactate, potassium lactate, or calcium lactate.

(16) The method of any one of items 4 to 15, wherein a pH of a liquid after adding the aqueous solution B is 3.2 or greater and less than 7.0.
(17) The method of any one of items 4 to 16, wherein a pH of a liquid after adding the aqueous solution B is 4.0 or greater and less than 7.0.
(18) The method of any one of items 4 to 17, wherein a pH of a liquid after adding the aqueous solution B is 5.0 or greater and less than 7.0.
(19) The method of any one of items 1 to 18, wherein the chlorine dioxide is present at a concentration of 0.8 to 1.0%.
(20) A chlorous acid aqueous solution manufactured by a method comprising the step of trapping chlorine dioxide ($ClO_2$) with aqueous solution A comprising one of an inorganic acid, inorganic acid salt, organic acid, and organic acid salt, two or more types thereof or a combination thereof.
(21) The chlorous acid aqueous solution of item 20, wherein the method further comprises a step of adding the chlorine dioxide in the presence of hydrogen peroxide.
(22) The chlorous acid aqueous solution of item 20 or 21, wherein a pH of the aqueous solution A is 11.0 or less and 6.0 or greater.
(23) The chlorous acid aqueous solution of any one of items 20 to 22, wherein a pH of the aqueous solution A is 10.8 or less and 10.2 or greater.
(24)
The chlorous acid aqueous solution of any one of items 20 to 22, wherein the chlorine dioxide ($ClO_2$) is provided as gas.

Additional embodiments and advantages of the present invention are recognized by those skilled in the art who read and understand the following detailed description as needed.

Advantageous Effects of Invention

According to the present invention, a technique is provided for stabilizing chlorous acid, which is a useful substance, in an aqueous solution for a long period of time, such that the possibility of utility has improved as a chlorous acid aqueous solution that is convenient for handling in a wide range of applications in not only the food industry, but also in many fields such as welfare and nursing facilities and medical facilities.

DESCRIPTION OF EMBODIMENTS

Figure 1:
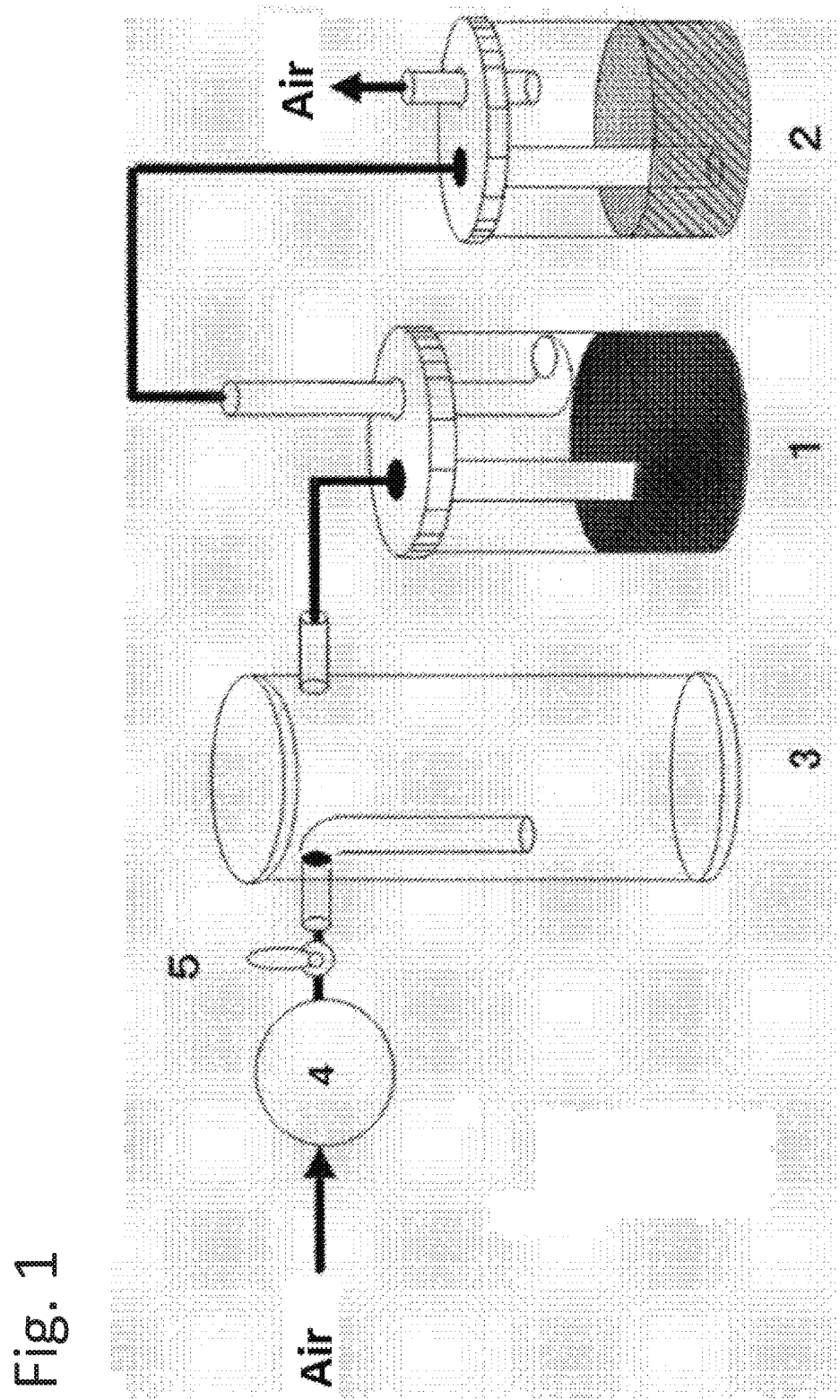
FIG. 1 shows a schematic diagram of a manufacturing plant used in the Examples. Each symbol represents the following: 1: chlorous acid aqueous solution manufacturing tank; 2: gas washing device; 3: chlorine dioxide gas storage tank; 4: air pump; 5: air flow spigot.

The present invention is described hereinafter. Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

As used herein "chlorous acid aqueous solution" refers to an aqueous solution comprising chlorous acid ($HClO_2$) that is used as a sterilizing agent. The chlorous acid aqueous solution of the present invention creates a transitional state and delays a decomposition reaction, such that chlorous acid ($HClO_2$) can be stably maintained over a long period of time. When a sample of chlorous acid aqueous solution is measured with a spectrophotometer, the presence of a chlorous acid aqueous solution can be confirmed when an absorbent section comprising an acidic chlorite ion ($H^+ + ClO_2^-$) representing a peak near 260 nm and an absorbent section comprising chlorine dioxide ($ClO_2$) representing a peak near 350 nm can be simultaneously confirmed between wavelengths 240 to 420 nm in the UV spectrum, i.e., when a double peak is exhibited. In such a case, it is understood that a cyclic reaction involving the main constituent chlorous acid ($HClO_2$), chlorine dioxide ($ClO_2$), and acidic chlorite ion ($H^+ + ClO_2^-$) is simultaneously in progress.

As used herein, the term "chlorous acid aqueous solution" may encompass a "chlorous acid aqueous solution formulation". A chlorous acid aqueous solution formulation can be manufactured by using a chlorous acid aqueous solution manufactured by the manufacturing method of the present invention and blending in aqueous solution B. A representative constitution of a chlorous acid aqueous solution formulation that can be mixed and used is 60.00% (w/v) chlorous acid aqueous solution (5% product) (chlorous acid concentration is 50000 ppm), 1.70% (w/v) potassium dihydrogen phosphate, 0.50% (w/v) potassium hydroxide, and 37.8% purified water (sold under the name "AUTOLOC Super" by the Applicant), but the constitution is not limited thereto. When this constitution of mixture is used, the chlorous acid aqueous solution may be 0.25% (w/v) to 75% (w/v), potassium dihydrogen phosphate may be 0.70% (w/v) to 13.90% (w/v), and potassium hydroxide may be 0.10% (w/v) to 5.60% (w/v). It is also possible to use sodium dihydrogen phosphate instead of potassium dihydrogen phosphate, and sodium hydroxide instead of potassium hydroxide.

As used herein, "stability" of a chlorous acid aqueous solution refers to a state of maintaining chlorous acid ($HClO_2$).

As used herein, "antimicrobial (action)" refers to suppression of growth of pathogenic, harmful, or infectious microorganisms such as mold, microbes, or viruses. A substance having antimicrobial action is referred to as an antimicrobial agent.

As used herein, "sterilizing (action)" refers to killing of pathogenic, harmful, or infectious microorganisms such as mold, microbes, or viruses. A substance having sterilizing action is referred to as a sterilizing agent.

As used herein, "microbe-removing (action)" refers to removal of pathogenic, harmful, or infectious microorganisms such as mold, microbes, or viruses. A substance having microbe-removing action is referred to as a micro-removing agent.

As used herein, "disinfecting (action)" refers to disinfection of pathogenic, harmful, or infectious microorganisms such as mold, microbes, or viruses. A substance having disinfecting action is referred to as a disinfecting agent.

Antimicrobial action, sterilizing action, microbe-removing action, and disinfecting action are collectively referred to as germicidal (action), which is used herein as a broad concept encompassing antimicrobial (action), sterilizing (action), microbe-removing (action), and disinfecting (action) unless specifically noted otherwise. Thus, substances having antimicrobial action, sterilizing action, microbe-removing action, or disinfecting action collectively referred herein as a "sterilizing agent", which is understood as an agent also having action corresponding to antimicrobial action, sterilizing action, microbe-removing action, and disinfecting action in general use herein.

As used herein, an article used with a manufactured chlorous acid aqueous solution is any article that can be impregnated with the chlorous acid aqueous solution to be used in sterilization or the like, including medical devices. Examples thereof include, but are not limited to, a sheet, film, patch, brush, nonwoven fabric, paper, fabric, absorbent cotton, sponge and the like. Further, any material may be used, as long as a chlorous acid aqueous solution can be impregnated therein.

As used herein, "TAL" is used to measure alkalinity of a sample by titrating 0.1 mol/L hydrochloric acid-standard acid solution until a sample has a pH of 4.0, wherein alkalinity (TAL) is 1 when 1 mL of 0.1 mol/L hydrochloric acid is required to make 100 g of sample to have a pH of 4.0. A pH of 4.0 is the second neutralization point for sodium carbonate.

(Chlorous Acid Aqueous Solution and Manufacturing Example Thereof)

The chlorous acid aqueous solution used in the present invention has a feature and function that was discovered by the inventors.

The present invention relates to a method that is different from known manufacturing methods, such as those described in Patent Literature 1.

Specifically, conventional techniques added and reacted sulfuric acid or an aqueous solution thereof, with an aqueous sodium chlorate solution, in an amount and concentration at which the pH value of the aqueous sodium chlorate solution can be maintained from 2.3 to 3.4 to generate chloric acid, and then added hydrogen peroxide in an amount equivalent to or greater than the amount required for a reduction reaction of the chloric acid. However, the feature of the present invention is accomplished by providing a method of manufacturing chlorous acid comprising the step of adding chlorine dioxide gas ($ClO_2$), instead of adding hydrogen peroxide to chloric acid, to one of an inorganic acid, inorganic acid salt, organic acid, and organic acid salt, two or more types thereof or a combination thereof (aqueous solution A). Use of chlorine dioxide gas (gas) is beneficial in that it generates chlorite ions with a high level of alkalinity and lowers the pH to neutral or lower, and then some of the chlorite ions transition to a state of chlorous acid to create a transitional state, resulting in delaying a decomposition reaction, such that chlorous acid ($HClO_2$) can be stably maintained over a long period of time. Such an effect can be accomplished by trapping chlorine dioxide ($ClO_2$) with aqueous solution A comprising one of an inorganic acid, inorganic acid salt, organic acid, and organic acid salt, two or more types thereof or a combination thereof. The expression "trap" may refer to adsorption, capture or the like, preferably any manipulation leading to co-existence of gaseous chlorine dioxide with one of an inorganic acid, inorganic acid salt, organic acid, and organic acid salt, two or more types thereof or a combination thereof. Examples of such a manipulation generally include, but are not limited to, a method of directly blowing in gas into aqueous solution A, a method of adsorption by spraying aqueous solution A like a mist from the top and releasing chlorine dioxide gas from the bottom, air blast and the like. Although not wishing to be bound by any theory, the chlorous acid aqueous solution of the present invention manufactured by using a manufacturing plant as shown in FIG. 1 (see Examples 1 to 6) is demonstrated as exhibiting a stable sterilizing effect at least under refrigerated condition (4° C.) for 10 days as shown in Example 7. Thus, the present invention is understood as providing a manufacturing method of stable chlorous acid in an aqueous solution, the so-called chlorous acid aqueous solution.

A chlorous acid aqueous solution formulation can be manufactured by mixing in aqueous solution B with a chlorous acid aqueous solution manufactured by the manufacturing method of the present invention. A representative constitution of such a formulation that can be mixed and used is, for example, 60.00% (w/v) chlorous acid aqueous solution (5% product) (chlorous acid concentration is 50000 ppm), 1.70% (w/v) potassium dihydrogen phosphate, 0.50% (w/v) potassium hydroxide, and 37.8% purified water (sold under the name "AUTOLOC Super" by the Applicant), but the constitution is not limited thereto. When this constitution of mixture is used, the chlorous acid aqueous solution may be 0.25% (w/v) to 75% (w/v), potassium dihydrogen phosphate may be 0.70% (w/v) to 13.90% (w/v), and potassium hydroxide may be 0.10% (w/v) to 5.60% (w/v). It is also possible to use sodium dihydrogen phosphate instead of potassium dihydrogen phosphate, and sodium hydroxide instead of potassium hydroxide. Although this agent reduces the deterioration of chlorous acid due to contact with an organic matter under acidic conditions, the sterilizing effect is maintained. In addition, very little chlorine gas is generated. The agent also has a feature of generating an insignificant amount of chlorine gas, thus reducing amplification of chlorine odor generated from reacting chlorine with an organic matter.

Conventional manufacturing methods generate a chlorous acid aqueous solution by adding and reacting sulfuric acid or an aqueous solution thereof, with an aqueous sodium chlorate solution, in an amount and concentration at which the pH value of the aqueous sodium chlorate solution can be maintained at 3.4 or lower to generate chloric acid, and then adding hydrogen peroxide in an amount equivalent to or greater than the amount required for a reduction reaction of the chloric acid. The present invention is significantly different in terms of the use of chlorine dioxide gas. A difference is also found in the use of chlorine dioxide gas creating a transitional state and delaying a decomposition reaction, such that chlorous acid ($HClO_2$) can be stably maintained over a long period of time. In addition, the present invention is characterized in that a raw material for generating chlorine dioxide gas does not need to be specified by utilizing chlorine dioxide as the raw material. For instance, chlorine dioxide gas is generated in addition to acidified sodium chlorite (ASC) when sodium chlorite is added to acid. However, such chlorine dioxide gas can be utilized to manufacture a chlorous acid aqueous solution. Sodium chlorite is a highly alkaline substance that is integrated with an alkaline substance to be stable. Sodium chlorite needs to be in a state of acidified sodium chlorite (ASC) to exert an effect for use as a sterilizing agent. However, use of this method can also lead to manufacture of a chlorous acid aqueous solution, which is a liquid product, by using as a raw material, a gasified chlorine dioxide separately generated from acidified sodium chlorite, which is a liquid product. Furthermore, due to the electrolysis process in the manufacture of a chlorous acid aqueous solution from sodium chloride, there was a risk of bromide ions in the sodium chloride changing into a carcinogenic substance bromic acid and contaminating the chlorous acid aqueous solution. However, since the manufacturing method of the present invention uses chlorine dioxide gas which is gas, such a risk of carcinogenic substance contamination has been eliminated. Use of chlorine dioxide gas as a raw material is characterized in further facilitating the manufacture of chlorous acid aqueous solution because there would be no need to consider the preceding process. In addition, since generation of chlorine dioxide gas is not preferable in a manufacturing method from sodium chlorite, it is considered desirable to increase alkalinity. A pH closer to is considered more preferable. Thus, a method of manufacturing sodium chlorite is recognized as performing the complete opposite of the present method, which manufactures a chlorous acid aqueous solution by using aqueous solution A, which is neutral to weakly alkaline, e.g., pH of 6.0 to the order of 11.0 shown in the present invention.

In one embodiment, the chlorine dioxide gas ($ClO_2$) is provided as gas. In a specific embodiment, chlorine dioxide gas ($ClO_2$) is gas that is used with a concentration of 0.8 to 1.0% (e.g., the acceptable range is 0.9%±0.1%). One preferred concentration is 0.88%, but is not limited thereto. Gas with a high concentration is dangerous due to its explosiveness. Thus, such gas is diluted with nitrogen gas or the like for use.

In one embodiment, the chlorine dioxide gas is added in the presence of hydrogen peroxide ($H_2O_2$). In another embodiment, the aqueous solution A may contain hydrogen peroxide, and the chlorine dioxide gas is trapped with aqueous solution A containing hydrogen peroxide. Coexistence of chlorine dioxide gas with hydrogen peroxide ($H_2O_2$) suppresses the generation of chlorate ions and generates chlorous acid ($HClO_2$) through the so-called "cyclic reaction" where chlorite ions, chlorous acid, and aqueous chlorine dioxide are simultaneously present.

A preferred embodiment comprises, after the step of adding, the step of further adding one of an inorganic acid, inorganic acid salt, organic acid, and organic acid salt, two or more types thereof or a combination thereof. This is because the pH or the like can be adjusted to adjust the transitional state by further adding a step in this manner.

Further, in another embodiment, carbonic acid, phosphoric acid, boric acid, or sulfuric acid can be used as inorganic acid in the above-described method, but phosphoric acid is preferred. Although not wishing to be bound by any theory, the present invention is demonstrated as being able to be maintained within a suitable range of pH with a high buffering effect in a state of chlorous acid while retaining a sterilizing effect by using especially phosphoric acid.

Furthermore, in another embodiment, carbonate, hydroxide, phosphate, or borate can be used as inorganic acid salt, but phosphate is preferred. Although not wishing to be bound by any theory, the present invention is demonstrated as being able to be maintained within a suitable range of pH with a high buffering effect in a state of chlorous acid while retaining a sterilizing effect by using especially phosphate.

Further, in another embodiment, sodium carbonate, potassium carbonate, sodium bicarbonate, or potassium bicarbonate may be used as carbonate, but sodium carbonate is preferred. This is because pH has buffering power at a weakly alkaline region and weakly acidic region, such that chlorous acid can be advantageously stabilized in this region.

Furthermore, in another embodiment, sodium hydroxide, potassium hydroxide, calcium hydroxide, or barium hydroxide may be used as hydroxide, but potassium hydroxide or sodium hydroxide is preferred. Although not wishing to be bound by any theory, such hydroxides can be used to increase chlorous acid content. Meanwhile, use of a divalent salt may be advantageous because desalination is possible in combined use with phosphoric acid such that the amount of salt to chlorous acid and chlorite ions can be reduced.

Furthermore, in another embodiment, disodium hydrogen phosphate, sodium dihydrogen phosphate, trisodium phosphate, tripotassium phosphate, dipotassium hydrogen phosphate, or potassium dihydrogen phosphate may be used as the phosphate. Preferably, dipotassium hydrogen phosphate can be used. Although not wishing to be bound by any theory, this is because these phosphates can have buffering power in a useful pH region exerting the most sterilization power, which is a pH from 5 to less than 7. This can be advantageous because chlorous acid can be stable in this pH region.

Further, in another embodiment, sodium borate or potassium borate can be used as borate.

Furthermore, in another embodiment, succinic acid, citric acid, malic acid, acetic acid, lactic acid can be used as organic acid. Succinic acid can be preferably used. Although not wishing to be bound by any theory, succinic acid can have buffering power from a pH of less than 6 to 4. Drastic gasification of chlorine dioxide can be suppressed within this range of pH. However, pH tends to drastically decrease when pH is less than 5, in which case use of organic acid with a buffering power with a pH from 3 to less than 4 such as citric acid is desirable.

Furthermore, in another embodiment, sodium succinate, potassium succinate, sodium citrate, potassium citrate, sodium malate, potassium malate, sodium acetate, potassium acetate, sodium lactate, potassium lactate, or calcium lactate can be used as organic acid salt.

In one embodiment, the advantageous initial pH of a buffering agent with chlorine dioxide blown therein is generally, but not limited to, 11.0 or less and 6.0 or greater, and more preferably 10.8 or less and 10.2 or greater. When the initial pH is 10.8 or less and 10.2 or greater, the available chlorine concentration ultimately attained increases while suppressing generation of chlorite and the yield is improved. As used herein, pH values are rounded to indicate one significant digit. For instance, when the actual measured value is a pH of 10.83, this value is shown as a pH of 10.8.

Normally, such a pH may be 11.0 or greater, where available chlorine concentration ultimately attained increases and the yield is improved. However, use of sodium hydroxide (caustic soda) or the like is not preferable because the use would generate sodium chlorite, which is contradictory to the objective of the present invention. Although not wishing to be bound by any theory, when sodium chlorite is manufactured, chlorine dioxide gas is adsorbed to an aqueous solution in which hydrogen peroxide is added to a high concentration of sodium hydroxide. The pH of the aqueous solution prior to adsorption to chlorine dioxide gas is strongly alkaline with a pH of 11.3 or greater and 12 or greater in practice. The recovery rate would be nearly 100%. Thus, one adsorption tank is sufficient (generally two or more adsorption tanks are required as the recovery rate is low for chlorous acid aqueous solution), where the generated product is not chlorous acid aqueous solution but sodium chlorite. Thus, such a pH suitable for the objective of the present invention may be any condition that chlorine dioxide gas could have. A typical example includes, but is not limited to, a pH of 6.0 to 11.0 and preferably 10.2 to 10.8. Examples of a preferably pH as an upper limit include, but not limited to, 11.2, 11.1, 11.0, 10.9, 10.8, 10.7, 10.6, 10.5, 10.4, 10.3, 10.2, 10.1, 10.0, 9.9, 9.8, 9.7, 9.6, 9.5, 9.4, 9.3, 9.2, 9.1, 9.0 and the like. Examples of preferred upper limits of pH include a value less than 11, value less than 10.5, value less than 10, value less than 9.5, value less than 9, value less than 8.5, value less than 8, value less than 7.5, value less than 7, value less than 6.5 and the like. Examples of preferred low limit of pH include, but are not limited to, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2 and the like. Examples of preferred lower limit of pH include a value greater than 6, value greater than 6.5, value greater than 7, value greater than 7.5, value greater than 8, value greater than 8.5, value greater than 9, value greater than 9.5, value greater than 10 and the like. Any combination of such upper limits and lower limits can be suitable and used in the present invention. Examples of preferred combinations of an upper limit and lower limit include 6.0 to 6.5, 6.0 to value less than 6.5, 6.0 to 9.0, 6.0 to value less than 9.0, 6.0 to 10.0, 6.0 to value less than 10.0, 6.0 to 11.0, 6.0 to value less than 11.0, value greater than 6.0 to value of 6.5, value greater than 6.0 to value of 9.0, value greater than 6.0 to value of 10.0, value greater than 6.0 to value of 11.0, value greater than 6.0 to value less than 6.5, value greater than 6.0 to value less than 9.0, value greater than 6.0 to value less than 10.0, value greater than 6.0 to value less than 11.0, 7.0 to 9.0, 7.0 to value less than 9.0, 7.0 to 10.0, 7.0 to value less than 10.0, 7.0 to 11.0, 7.0 to value less than 11.0, value greater than 7.0 to value of 9.0, value greater than 7.0 to value of 11.0, value greater than 7.0 to value less than 9.0, value greater than 7.0 to value less than 11.0 and the like.

When chlorine dioxide gas is adsorbed to a low concentration aqueous alkaline solution in the manufacture of a chlorous acid aqueous solution, a small buffer zone appears between pH of 6 and 8 (normal sodium chlorite does not have such a buffer zone). A buffering agent for retaining a potent buffering power in this pH region is required to maintain what is in this buffer region in a state of chlorous acid or chlorite ion for a long period of time. Thus, a buffering agent and a range of pH that fit this condition are preferably selected.

Although the sodium chlorite content can be increased more with stronger buffering power from pH 14 to pH of 10, the manufacturing method of the present invention is for manufacturing an aqueous solution that maintains a cyclic reaction of chlorous acid, chlorine dioxide and chlorite ion. Thus, there is no need to raise the initial pH of aqueous solution A, which is strongly alkaline required to manufacture sodium chlorite, to a pH of 11.0 or greater. Since the present invention is not a method of manufacturing sodium chlorite, it is preferable to avoid a condition under which sodium chlorite is produced. Although not wishing to be bound by any theory, it is important for the present invention to enhance buffering power from the neutral to the weakly acidic region, and thus TAL (provided that the initial value is pH of 11.0 or less) was employed as an indicator thereof. When the pH of the manufactured chlorous acid aqueous solution is low, a buffering agent may be newly added to raise the pH. In one embodiment, when the manufactured chlorous acid aqueous solution is used and mixed with a buffering agent, the pH range may be 3.2 to 7.0.

Although there is currently no concentration that is necessarily optimal as the concentration of the blown in chlorine dioxide gas, one embodiment can use gas with a concentration of 0.8 to 1.0% and a specific example can use gas with a concentration of 0.88%. Although not wishing to be bound by any theory, gas with a high concentration is dangerous due to its explosiveness. Thus, such gas is generally diluted with nitrogen gas or the like for use.

A conventional method of manufacturing an aqueous solution (chlorous acid aqueous solution) comprising chlorous acid ($HClO_2$) that can be used as a sterilizing agent would generate chlorous acid ($HClO_2$) by adding hydrogen peroxide ($H_2O_2$), to an aqueous solution of sodium chlorate ($NaClO_3$), in an amount required to produce chlorous acid by a reducing reaction of chloric acid ($HClO_3$) obtained by adding sulfuric acid ($H_2SO_4$) or an aqueous solution thereof to an aqueous solution of sodium chlorate ($NaClO_3$) so that the aqueous solution of sodium chlorate is in an acidic condition. The basic chemical reaction of this method of manufacturing is represented by the following formula A and formula B.

[Chemical 1]

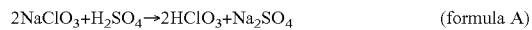

$$2NaClO_3 + H_2SO_4 \rightarrow 2HClO_3 + Na_2SO_4 \quad \text{(formula A)}$$

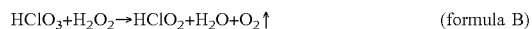

$$HClO_3 + H_2O_2 \rightarrow HClO_2 + H_2O + O_2\uparrow \quad \text{(formula B)}$$

Formula A indicates that chloric acid is obtained while sodium ions are removed by adding sulfuric acid ($H_2SO_4$) or an aqueous solution thereof in an amount and concentration at which the pH value of an aqueous sodium chlorate ($NaClO_3$) solution can be maintained within acidity. Next, formula B indicates that chloric acid ($HClO_3$) is reduced with hydrogen peroxide ($H_2O_2$) to produce chlorous acid ($HClO_2$).

[Chemical 2]

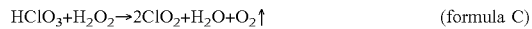

$$HClO_3 + H_2O_2 \rightarrow 2ClO_2 + H_2O + O_2\uparrow \quad \text{(formula C)}$$

$$2ClO_2 + H_2O_2 \rightarrow 2HClO_2 + O_2\uparrow \quad \text{(formula D)}$$

$$2ClO_2 + H_2O \leftrightarrow HClO_2 + HClO_3 \quad \text{(formula E)}$$

$$2HClO_2 \leftrightarrow H_2O + Cl_2O_3 \quad \text{(formula F)}$$

At this time, chlorine dioxide gas ($ClO_2$) is generated (formula C). However, coexistence with hydrogen peroxide ($H_2O_2$) results in the production of chlorous acid ($HClO_2$) through the reactions in formulae D-F. The present invention utilizes the reactions after the chlorine dioxide gas ($ClO_2$). Although not wishing to be bound by any theory, when this reaction was taken out and utilized, it was unexpectedly found that it is possible to create a transitional state and delay a decomposition reaction, such that chlorous acid ($HClO_2$) can be stably maintained over a long period of time.

Meanwhile, the property of the produced chlorous acid ($HClO_2$) is such that it is decomposed early into chlorine dioxide gas or chlorine gas due to the presence of chloride ion ($Cl^-$), hypochlorous acid (HClO) and other reduction substances or a decomposition reaction occurring among a plurality of chlorous acid molecules. Thus, it is necessary to prepare chlorous acid ($HClO_2$) such that the state of being chlorous acid ($HClO_2$) can be maintained for a long period of time in order to be useful as a sterilizing agent.

In this regard, chlorous acid ($HClO_2$) can be stably maintained over a long period of time by adding one of an inorganic acid, inorganic acid salt, organic acid, and organic acid salt, two or more types thereof or a combination thereof to the chlorous acid ($HClO_2$), chlorine dioxide gas ($ClO_2$) or an aqueous solution containing them obtained by the above-described method to create a transitional state and delay a decomposition reaction. Although not wishing to be bound by any theory, the present invention further demonstrates that a transitional state is created and a decomposition reaction is delayed such that chlorous acid ($HClO_2$) can be stably maintained over a long period of time by using, for example, a phosphoric acid buffering agent. Furthermore, although not wishing to be bound by any theory, the present invention demonstrates that a longer and more stable transitional state can be created and chlorous acid ($HClO_2$) can be maintained over a longer period of time by delaying a decomposition reaction when using potassium salt (potassium hydroxide, potassium phosphate salt (e.g., tripotassium phosphate, dipotassium hydrogen phosphate, or potassium dihydrogen phosphate)) as metal, in comparison to cases using sodium salt (e.g., sodium hydroxide, sodium phosphate salt (disodium hydrogen phosphate, sodium dihydrogen phosphate, trisodium phosphate) as metal.

In one embodiment, it is possible to utilize chlorous acid ($HClO_2$), chlorine dioxide gas ($ClO_2$), or an aqueous solution containing them obtained by the above-described method, to which one of an inorganic acid and inorganic acid salt, specifically phosphate, carbonate and hydroxide, particularly phosphate and hydroxide, two or more types thereof or a combination thereof is added.

In another embodiment, it is possible to utilize an aqueous solution to which one of an inorganic acid and inorganic acid salt, specifically phosphate, carbonate and hydroxide, particularly phosphate and hydroxide, two or more types thereof or a combination thereof is added, to which one of an inorganic acid, inorganic acid salt, organic acid, and organic acid salt, two or more types thereof or a combination thereof is added.

Additionally, in another embodiment, it is possible to utilize an aqueous solution manufactured by the above-described method, to which one of an inorganic acid, inorganic acid salt, organic acid, and organic acid salt, two or more types thereof or a combination thereof is added.

Examples of inorganic acid include, but are not limited to, carbonic acid, phosphoric acid, boric acid, and sulfuric acid, while phosphoric acid is preferable. Further, examples of inorganic salt include, but are not limited to, carbonate and hydroxide as well as phosphate and borate, where phosphate is preferable. More specifically, sodium carbonate, potassium carbonate, sodium bicarbonate, potassium bicarbonate, or the like may be used as the carbonate; sodium hydroxide, potassium hydroxide, calcium hydroxide, barium hydroxide, or the like may be used as the hydroxide; disodium hydrogen phosphate, sodium dihydrogen phosphate, trisodium phosphate, tripotassium phosphate, dipotassium hydrogen phosphate, potassium dihydrogen phosphate, or the like may be used as the phosphate; and sodium borate, potassium borate, or the like may be used as the borate, which is preferably, but not limited to, potassium salt. Furthermore, examples of the above-described organic acid include succinic acid, citric acid, malic acid, acetic acid, lactic acid and the like. Further, sodium succinate, potassium succinate, sodium citrate, potassium citrate, sodium malate, potassium malate, sodium acetate, potassium acetate, sodium lactate, potassium lactate, calcium lactate or the like is suitable as the organic acid salt.

When an acid and/or a salt thereof is added, a transitional state, such as $Na^+ + ClO_2^- <\text{-->} Na\text{---}ClO_2$, $K^+ + ClO_2^- <\text{-->} K\text{---}ClO_2$, or $H^+ + ClO_2^- <\text{-->} H\text{---}ClO_2$ can be temporarily created to delay the progression of chlorous acid ($HClO_2$) to chlorine dioxide ($ClO_2$), which enables the manufacture of an aqueous solution comprising chlorous acid ($HClO_2$) that maintains chlorous acid ($HClO_2$) for a long period of time and generates a small amount of chlorine dioxide ($ClO_2$). Although not wishing to be bound by any theory, it was demonstrated in the present invention that such an effect of maintaining is enhanced by using a phosphoric acid buffering agent. Although not wishing to be bound by any theory, it was further demonstrated in the present invention that such an effect of maintaining is further enhanced by using potassium salt relative to a case of using sodium salt or the like.

The following represents the decomposition of chlorite in an acidic solution in the above-described chemical formula 2.

[Chemical 3]

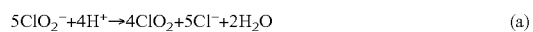

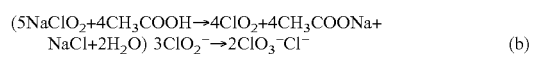

As represented in the formula, the rate of decomposition of an aqueous sodium chlorite solution in terms of pH is higher when pH is lower, i.e., when acidity is stronger. That is, the absolute rates of the reactions (a), (b), and (c) in the above-described formula increase. For example, although the ratio accounted for by reaction (a) decreases for a lower pH, the total decomposition rate changes significantly, i.e., increases. Thus, the amount of generated chlorine dioxide ($ClO_2$) increases with the decrease in pH. Thus, the lower the pH value results in earlier sterilization or bleaching. However, stimulatory and harmful chlorine dioxide gas ($ClO_2$) renders an operation difficult and negatively affects the health of a human being. Further, a reaction from chlorous acid to chlorine dioxide progresses quickly, resulting in the chlorous acid becoming unstable. In addition, the time a sterilization power is maintained is very short.

In this regard, when the above-described inorganic acid, inorganic acid salt, organic acid or organic acid salt is added to an aqueous solution comprising chlorous acid ($HClO_2$), pH values are adjusted within the range of 3.2 to 8.5, or within a preferred range such as pH 3.2 to 7.0 or pH 5.0 to 7.0 in accordance with the objective, from the viewpoint of balancing suppression of chlorine dioxide generation and sterilizing power.

When a spectrometric measurement of a sample can simultaneously identify an absorbent section comprising an acidic chlorite ion ($H^+ + ClO_2^-$) representing a peak near 260 nm and an absorbent section comprising chlorine dioxide ($ClO_2$) representing a peak near 350 nm between wavelengths 240 to 420 nm, it is possible to recognize presence of the chlorous acid aqueous solution of the present invention, i.e., the presence of chlorous acid ($HClO_2$). This is because a cyclic reaction involving the main constituent chlorous acid ($HClO_2$), chlorine dioxide ($ClO_2$), and acidic chlorite ion ($H^+ + ClO_2^-$) is simultaneously in progress as shown in the following Chemical Formula 4.

Cyclic reaction of chlorous acid, chlorine dioxide, and acidic chlorite ion

[Chemical 4]

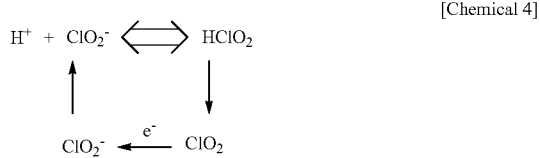

Conversion of chlorous acid ($HClO_2$) to chlorine dioxide ($ClO_2$) results in a single peak only near 350 nm.

It has already been found that pH can be further stabilized at this time by directly adding a buffering agent or by first adjusting the pH with sodium carbonate or the like and then adding another buffering agent.

Thus, in one aspect, the present invention provides a sterilizing agent comprising a chlorous acid aqueous solution, metal hydroxide, and metal phosphate.

Although not wishing to be bound by any theory, it was discovered that the present invention unexpectedly maintains a sterilizing effect while achieving an effect of long-term storage/stability because a combination of chlorine dioxide and one of an inorganic acid, inorganic acid salt, organic acid, and organic acid salt, two or more types thereof or a combination thereof creates a transitional state and delay a decomposition reaction such that chlorous acid ($HClO_2$) can be stably maintained in water over a long period of time. Examples of preferable ranges of pH include, but are not limited to, 3.2 or higher to less than 7.0, about 5.0 to about 7.5, about 5.0 to about 7.0, about 5.5 to about 7.0, about 5.0 to about 6.0, and the like. Examples of the lower limit include, but are not limited to, about 5.0, about 5.1, about 5.2, about 5.3, about 5.4, about 5.5, and the like, and examples of the upper limit include, but are not limited to, about 7.5, about 7.4, about 7.3, about 7.2, about 7.1, about 7.0, about 6.9, about 6.8, about 6.7, about 6.5, about 6.4, about 6.3, about 6.2, about 6.1, about 6.0, about 5.9, about 5.8, about 5.7, about 5.6, about 5.5, and the like. The optimal pH includes, but is not limited to, about 5.5. When "about" is used for a pH value herein, the range is intended to span 0.05 in both directions when the significant digit is the first decimal point. For example, about 5.5 is understood as referring to 5.45 to 5.55. For the purpose of distinction from sodium chlorite, pH is preferably, but not limited to, less than 7.0 in the present invention.

In another aspect, although not wishing to be bound by any theory, use of potassium salt is preferable in the present invention because the property of being readily dissociable in an aqueous solution by using potassium as metal in a phosphoric acid buffering agent relative to sodium or the like was found to be effective in maintaining chlorous acid, and the use was found to enhance an effect of maintaining the created transitional state for a long period of time and delaying the progression from chlorous acid ($HClO_2$) to chlorine dioxide ($ClO_2$).

Preferable metal hydroxide includes sodium hydroxide and/or potassium hydroxide. Preferable metal phosphate includes sodium phosphate (e.g., disodium hydrogen phosphate, sodium dihydrogen phosphate, trisodium phosphate) and/or potassium phosphate (e.g., tripotassium phosphate, dipotassium hydrogen phosphate, and potassium dihydrogen phosphate; especially potassium dihydrogen phosphate), and still preferably, potassium hydroxide and potassium phosphate (e.g., tripotassium phosphate, dipotassium hydrogen phosphate, and potassium dihydrogen phosphate; especially potassium dihydrogen phosphate), where the above are non-limiting examples.

In a preferred embodiment, sodium hydroxide and potassium hydroxide are 0.1 N to 1.0 N and buffer pH of sodium phosphate and potassium phosphate is 5.0 to 7.5, especially pH of 5.0 to 7.0. This is because the effect of long term storage/stability is unexpectedly enhanced more than the previously-expected levels at these constitution and pH.

In one aspect, the present invention provides a chlorous acid aqueous solution manufactured by a method comprising the step of trapping chlorine dioxide ($ClO_2$) with aqueous solution A comprising one of an inorganic acid, inorganic acid salt, organic acid, and organic acid salt, two or more types thereof or a combination thereof. In a preferred embodiment, the chlorous acid aqueous solution is manufactured by the method further comprising the step of adding the chlorine dioxide in the presence of hydrogen peroxide. In another preferred embodiment, the pH of the aqueous solution A is 11.0 or less and 6.0 or greater in the method. In still another preferred embodiment, the pH of the aqueous solution A is 10.8 or less and 10.2 or greater in the method. In another embodiment, the chlorine dioxide ($ClO_2$) is provided as gas in the method.

In one aspect, the present invention provides an article impregnated with the sterilizing agent of the present invention. An article that can be used as the article of the present invention is any article that can be impregnated with a chlorous acid aqueous solution to be used in sterilization or the like, including medical devices. Examples thereof include, but are not limited to, a sheet, film, patch, brush, nonwoven fabric, paper, fabric, absorbent cotton, sponge and the like.

Thus, the present invention provides, in one aspect, a kit for manufacturing a chlorous acid aqueous solution, comprising (1) a container comprising chlorine dioxide and (2) a container comprising one of an inorganic acid, inorganic acid salt, organic acid, and organic acid salt, two or more types thereof or a combination thereof.

In one preferred embodiment, the kit further comprises another (3) container comprising one of an inorganic acid, inorganic acid salt, organic acid, and organic acid salt, two or more types thereof or a combination thereof. (2) and (3) may be the same or different.

According to the present invention, chlorous acid ($HClO_2$) can be stably maintained over a long period of time. Although not wishing to be bound by any theory, this is because it is understood that use of chlorine dioxide can create a transitional state and delay a decomposition reaction. Thus, a chlorous acid aqueous solution manufactured by the present manufacturing method is considered to have a longer lifespan compared to conventional chlorous acid aqueous solutions.

According to the present invention, chlorous acid having a high level of sterilizing power can be stabilized for a long period of time. Thus, an aqueous solution comprising chlorous acid (so-called chlorous acid aqueous solution), which was generally difficult to distribute as a product, can now be distributed to the market and popularized in the society as a highly safe, useful and simple sterilizing agent.

Any reference document cited herein, such as a scientific article, patent or patent application, is incorporated herein by reference in the same manner as the entire content of each document is specifically described.

As described above, the present invention has been explained while presenting preferable embodiments to facilitate understanding. Hereinafter, the present invention is explained based on the Examples. However, the aforementioned explanation and the following Examples are provided solely for exemplification, not for limiting the present invention. Thus, the scope of the present invention is not limited to the Embodiments or Examples that are specifically described herein. The scope of the present invention is limited solely by the scope of the claims.

EXAMPLES

When necessary, animals used in the following Examples were handled in compliance with the Declaration of Helsinki. For reagents, the specific products described in the Examples were used. However, the reagents can be substituted with an equivalent product from another manufacturer (Sigma, Wako Pure Chemical, Nacalai Tesque, or the like). There are cases herein where an abbreviation "CAAS" is used for a chlorous acid aqueous solution. However, they are synonymous.

(Production Condition of Chlorous Acid Aqueous Solution)

The chlorous acid aqueous solution used in the following Examples is produced as explained below.

(Example of Manufacturing Plant)

An example of a manufacturing plant used is shown in FIG. 1.

Each of the numbers in FIG. 1 is the member shown in the following Table.

TABLE 1

| Number | Name |
|---|---|
| 1 | Chlorous acid aqueous solution manufacturing tank |
| 2 | Gas washing device |
| 3 | Chlorine dioxide gas storage tank |
| 4 | Air pump |
| 5 | Air flow spigot |

The chlorine dioxide gas used (made by the Applicant) has a concentration of 0.88%, and the acceptable range is preferably 0.9%±0.1%. Gas with a high concentration is dangerous due to its explosiveness. Thus, such gas is diluted with nitrogen gas or the like for use. Further, the flow rate can be adjusted with 5, which is set at 210 ppm/minute (210 ppm/min±40 ppm/min (660 mg·$ClO_2$/min to 530 mg·$ClO_2$/min)) in the present Example.

(Blending Examples for Each Solution)

Blending examples of each solution that can be used in the present manufacturing example are described below.

TABLE 2

Table of blended ingredients a (CAAS A-1)

| | Name of raw material | Blended amount |
|---|---|---|
| (1) | Tap water | 731.88 g |
| (2) | Sodium hydroxide | 2.5 g |
| (3) | Dipotassium hydrogenphosphate | 139.36 g |
| (4) | Sodium carbonate | 53 g |
| (5) | Sodium tetraborate (decahydrate) | 7.63 g |
| (6) | 35% hydrogen peroxide | 30 g |
| | Total | 1000 g |

TABLE 3

Table of blended ingredients b (CAAS A-2)

| | Name of raw material | Blended amount |
|---|---|---|
| (1) | Tap water | 738.64 g |
| (2) | Potassium hydroxide | 44.8 g |
| (3) | Dipotassium hydrogenphosphate | 139.36 g |
| (4) | Succinic acid | 47.2 g |
| (5) | 35% hydrogen peroxide | 30 g |
| | Total | 1000 g |

TABLE 4

Table of blended ingredients c (CAAS A-3)

| | Name of raw material | Blended amount |
|---|---|---|
| (1) | Tap water | 969 g |
| (2) | Sodium hydroxide | 1 g |
| (3) | 35% hydrogen peroxide | 30 g |
| | Total | 1000 g |

TABLE 5

Table of blended ingredient d (gas washing solution)

| | Name of raw material | Blended amount |
|---|---|---|
| (1) | Tap water | 910 g |
| (2) | Sodium hydroxide | 60 g |
| (3) | 35% hydrogen peroxide | 30 g |
| | Total | 1000 g |

Example 1: Manufacturing Example 1 of Chlorous Acid Aqueous Solution (CAAS A-1)

In Example 1, a chlorous acid aqueous solution was manufactured according to the following procedure based on the conditions for CAAS A-1 in (Production condition of chlorous acid aqueous solution).

(Method)

(1) Table of blended ingredient d was loaded into 2.
(2) Table of blended ingredient a was loaded into 1. The pH of the aqueous solution A was 10.8.
(3) A tank containing 0.9%±0.1% chlorine dioxide gas was prepared for 3.
(4) 4 was put into operation.
(5) 5 was released open to allow chlorine dioxide gas to flow into 1 at a flow rate of 210 ppm/minute (210 ppm/min±40 ppm/min (660 mg·$ClO_2$/min to 530 mg·$ClO_2$/min)).
(6) 5 was closed after the gas has flowed in for 15 minutes.
(7) 4 was stopped.
(8) The mixture was left standing for 15 minutes.

(9) 4 was again put into operation, and (4)-(8) were repeated 3 to 4 times (actual total time of chlorine dioxide gas flowing in was 45 to 60 minutes).

(10) The liquid in 1 was named chlorous acid aqueous solution A-1.

(Results)

The test results for the manufactured product are shown below.

TABLE 6

Chlorous acid aqueous solution A-1

| Tested item | Specification | Result |
| --- | --- | --- |
| Potassium permanganate | When potassium permanganate solution (1→300) is added to 5 ml of the present product (1→20), the mixture turns reddish purple. When 1 ml of sulfuric acid (1→20) is added thereto, the mixture turns light yellow. | When potassium permanganate solution (1→300) was added to 5 ml of the present product (1→20), the mixture turned reddish purple. When 1 ml of sulfuric acid (1→20) was added thereto, the mixture turned light yellow. |
| UV spectrum | An aqueous solution of the present product has maximum absorbance sections at wavelengths 258 to 262 nm and 346 to 361 nm. | An aqueous solution of the present product had maximum absorbance sections at wavelengths 258 to 262 nm and 346 to 361 nm. |
| Potassium iodide starch paper | When potassium iodide starch paper is immersed in the present product, the potassium iodide starch paper changes to a blue color and then the color fades. | When potassium iodide starch paper was immersed in the present product, the potassium iodide starch paper changed to a blue color and then the color faded. |
| Chlorous acid concentration | . . . | 58285 ppm |

Figure 2:
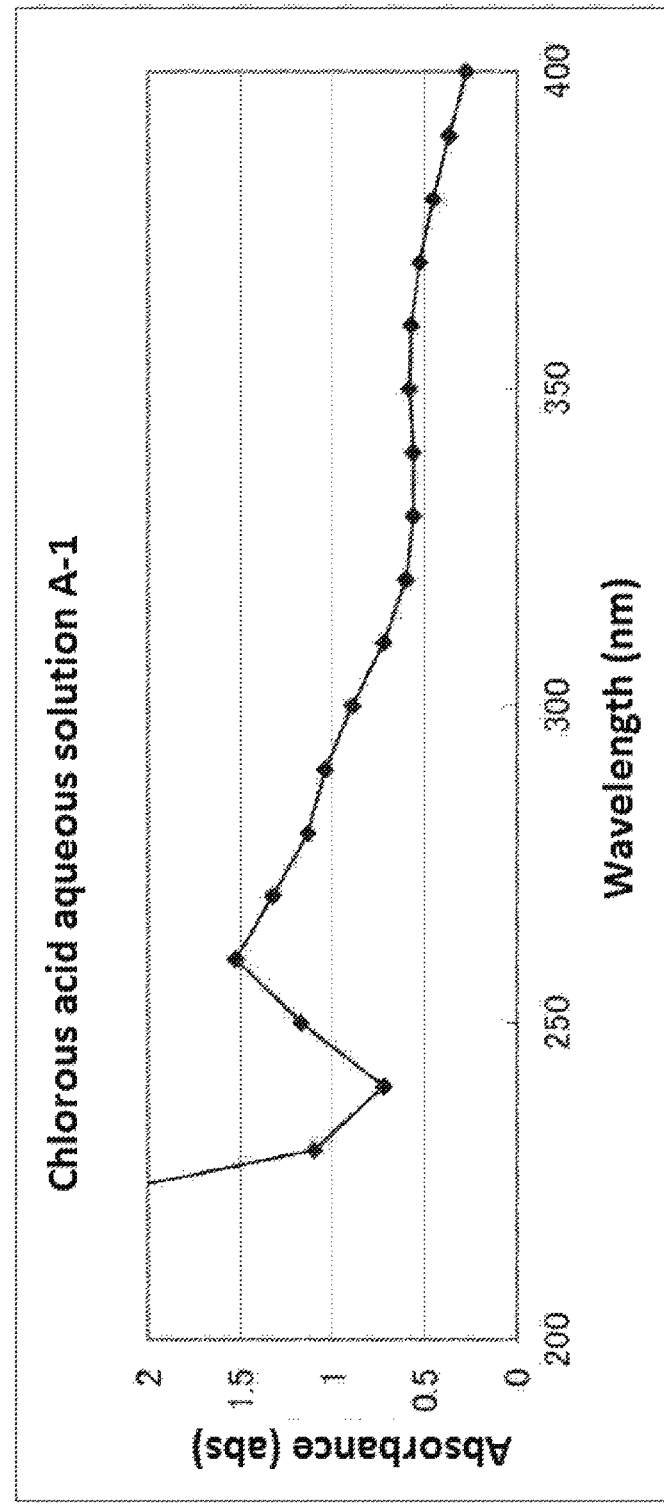
FIG. 2 shows the UV spectrum in Example 1. A double peak is observed.

The UV spectrum is shown in FIG. 2. The UV spectrum, as shown, has a double peak, confirming that a chlorous acid aqueous solution with a sterilizing effect retained is correctly manufactured.

Example 2: Manufacturing Example 1 of Chlorous Acid Aqueous Solution Formulation (CAAS A-1)

In Example 2, a chlorous acid aqueous solution formulation was manufactured according to the following procedure by using CAAS A-1 in Example 1.

Aqueous solution B was made based on the following.

TABLE 7

| | Name of raw material | Blended amount |
| --- | --- | --- |
| (1) | CAAS A-1 | 686.28 g |
| (2) | Dipotassium hydrogenphosphate | 14.00 g |
| (3) | Ion exchange water | 299.72 g |
| | Total | 1000 g |

The pH at this time was 6.4.

TABLE 8

Chlorous acid aqueous solution formulation A-1

| Tested item | Specification | Result |
| --- | --- | --- |
| Potassium permanganate | When potassium permanganate solution (1→300) is added to 5 ml of the present product (1→20), the mixture turns reddish purple. When 1 ml of sulfuric acid (1→20) is added thereto, the mixture turns light yellow. | When potassium permanganate solution (1→300) was added to 5 ml of the present product (1→20), the mixture turned reddish purple. When 1 ml of sulfuric acid (1→ 20) was added thereto, the mixture turned light yellow. |
| UV spectrum | An aqueous solution of the present product has maximum absorbance sections at wavelengths 258 to 262 nm and 346 to 361 nm. | An aqueous solution of the present product had maximum absorbance sections at wavelengths 258 to 262 nm and 346 to 361 nm. |
| Potassium iodide starch paper | When potassium iodide starch paper is immersed in the present product, the potassium iodide starch paper changes to a blue color and then the color fades. | When potassium iodide starch paper was immersed in the present product, the potassium iodide starch paper changed to a blue color and then the color faded. |
| Chlorous acid concentration | . . . | 40000 ppm |

Figure 3:
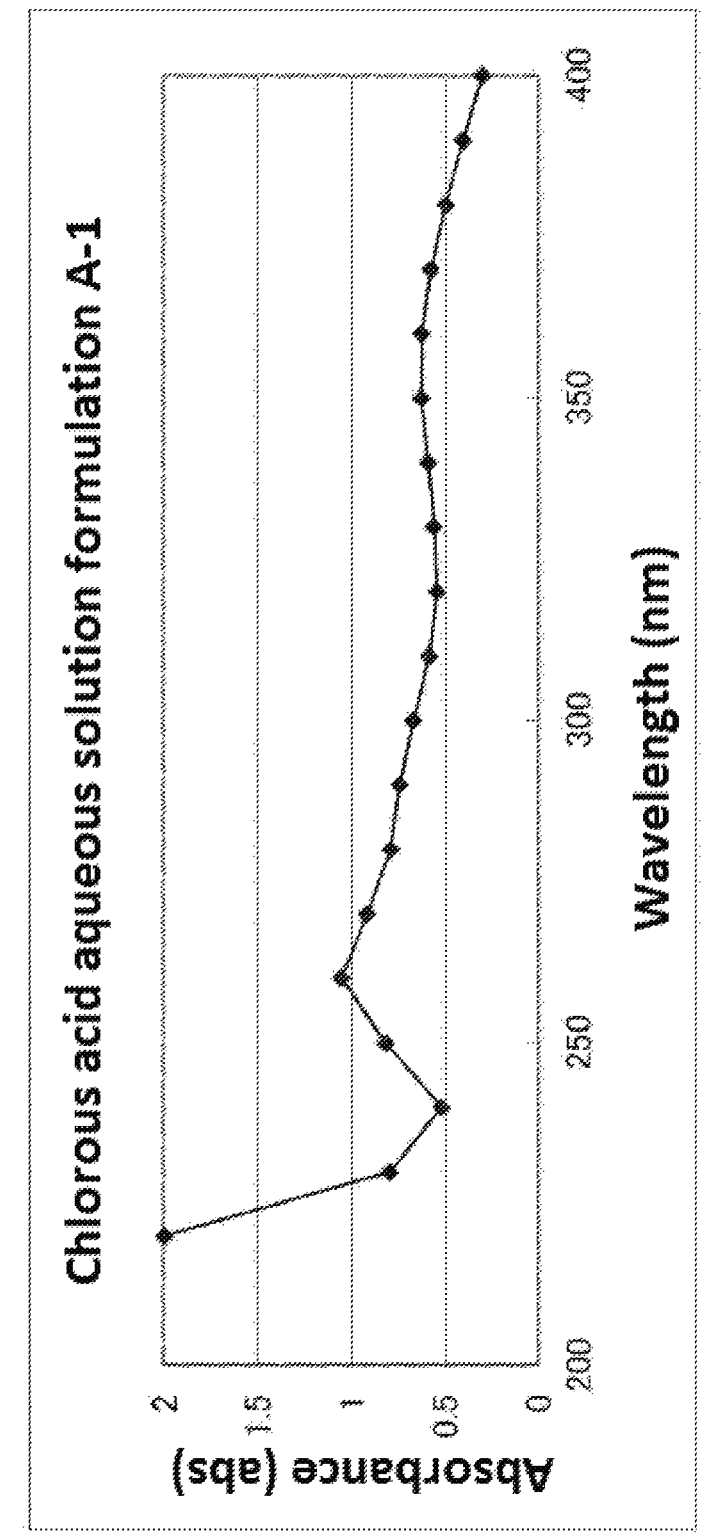
FIG. 3 shows the UV spectrum in Example 2. A double peak is observed.

The UV spectrum is shown in FIG. 3. The UV spectrum, as shown, has a double peak, confirming that a chlorous acid aqueous solution with a sterilizing effect retained is correctly manufactured.

Example 3: Manufacturing Example 2 of Chlorous Acid Aqueous Solution (CAAS A-2)

In Example 3, a chlorous acid aqueous solution was manufactured according to the following procedure based on the conditions for CAAS A-2 in (Production condition of chlorous acid aqueous solution).

(Method)

(1) Table of blended ingredient d was loaded into 2.

(2) Table of blended ingredient b was loaded into 1. The pH of the aqueous solution A was 8.0.

(3) A tank containing 0.9%±0.1% chlorine dioxide gas was prepared for 3.

(4) 4 was put into operation.

(5) 5 was released open to allow chlorine dioxide gas to flow into 1 at a flow rate of 210 ppm/minute (210 ppm/min±40 ppm/min (660 mg·$ClO_2$/min to 530 mg·$ClO_2$/min)).

(6) 5 was closed after the gas had flowed in for 15 minutes.

(7) 4 was stopped.

(8) The mixture was left standing for 15 minutes.

(9) 4 was again put into operation, and (4)-(8) were repeated 2 to 3 times (actual total time of chlorine dioxide gas flowing in was 30 to 45 minutes).

(10) The liquid in 1 was considered a chlorous acid aqueous solution.

The test results for the manufactured product are shown below.

TABLE 9

Table of blended ingredient b Chlorous acid aqueous solution A-2

| Tested item | Specification | Result |
|---|---|---|
| Potassium permanganate | When potassium permanganate solution (1→300) is added to 5 ml of the present product (1→20), the mixture turns reddish purple. When 1 ml of sulfuric acid (1→20) is added thereto, the mixture turns light yellow. | When potassium permanganate solution (1→300) was added to 5 ml of the present product (1→20), the mixture turned reddish purple. When 1 ml of sulfuric acid (1→20) was added thereto, the mixture turned light yellow. |
| UV spectrum | An aqueous solution of the present product has maximum absorbance sections at wavelengths 258 to 262 nm and 346 to 361 nm. | An aqueous solution of the present product had maximum absorbance sections at wavelengths 258 to 262 nm and 346 to 361 nm. |
| Potassium iodide starch paper | When potassium iodide starch paper is immersed in the present product, the potassium iodide starch paper changes to a blue color and then the color fades. | When potassium iodide starch paper was immersed in the present product, the potassium iodide starch paper changed to a blue color and then the color faded. |
| Chlorous acid concentration | . . . | 43093 ppm |

Figure 4:
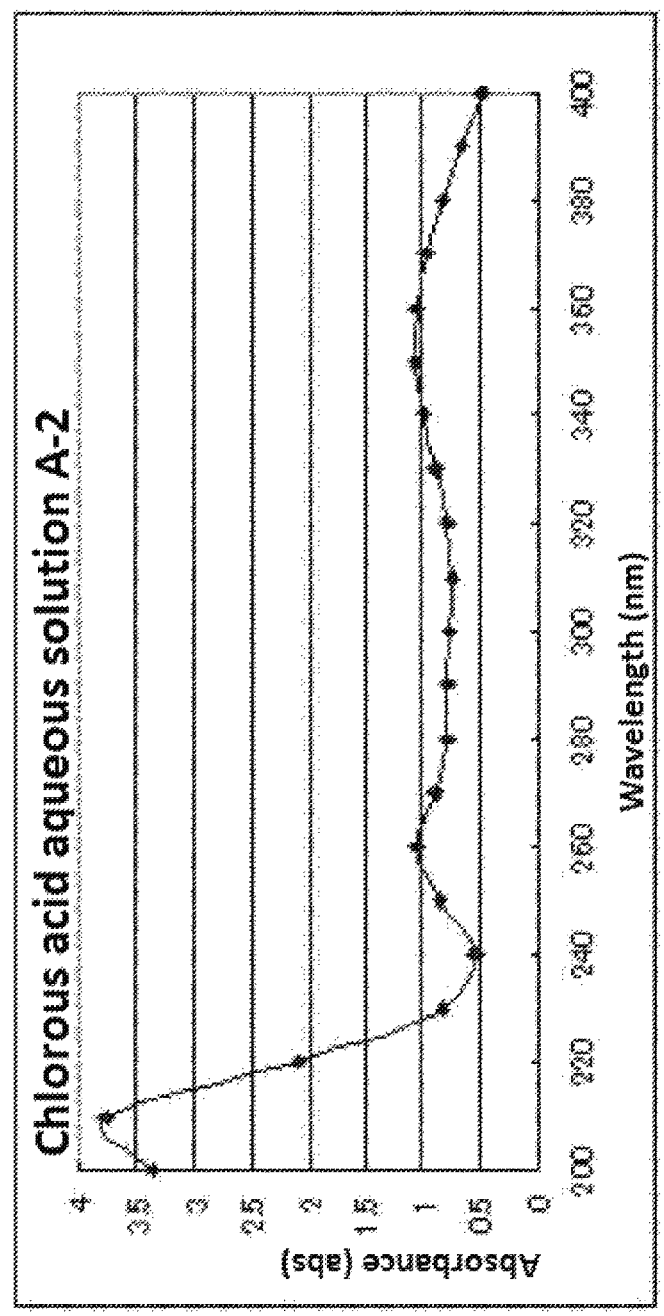
FIG. 4 shows the UV spectrum in Example 3. A double peak is observed.

The UV spectrum is shown in FIG. 4. The UV spectrum, as shown, has a double peak, confirming that a chlorous acid aqueous solution with a sterilizing effect retained is correctly manufactured.

Example 4: Manufacturing Example 2 of Chlorous Acid Aqueous Solution Formulation (CAAS A-2)

In Example 4, a chlorous acid aqueous solution formulation was manufactured according to the following procedure by using CAAS A-2 in Example 3.

Aqueous solution B was made based on the following.

TABLE 10

| | Name of raw material | Blended amount |
|---|---|---|
| (1) | Chlorous acid aqueous solution A-2 | 928.22 g |
| (2) | Potassium dihydrogenphosphate | 17.32 g |
| (3) | Ion exchange water | 54.46 g |
| | Total | 1000 g |

The pH at this time was 6.0.

TABLE 11

Chlorous acid aqueous solution formulation A-2

| Tested item | Specification | Result |
|---|---|---|
| Potassium permanganate | When potassium permanganate solution (1→300) is added to 5 ml of the present product (1→20), the mixture turns reddish purple. When 1 ml of sulfuric acid (1→20) is added thereto, the mixture turns light yellow. | When potassium permanganate solution (1→300) was added to 5 ml of the present product (1→20), the mixture turned reddish purple. When 1 ml of sulfuric acid (1→20) was added thereto, the mixture turned light yellow. |
| UV spectrum | An aqueous solution of the present product has maximum absorbance sections at wavelengths 258 to 262 nm and 346 to 361 nm. | An aqueous solution of the present product had maximum absorbance sections at wavelengths 258 to 262 nm and 346 to 361 nm. |
| Potassium iodide starch paper | When potassium iodide starch paper is immersed in the present product, the potassium iodide starch paper changes to a blue color and then the color fades. | When potassium iodide starch paper was immersed in the present product, the potassium iodide starch paper changed to a blue color and then the color faded. |
| Chlorous acid concentration | . . . | 40000 ppm |

Figure 5:
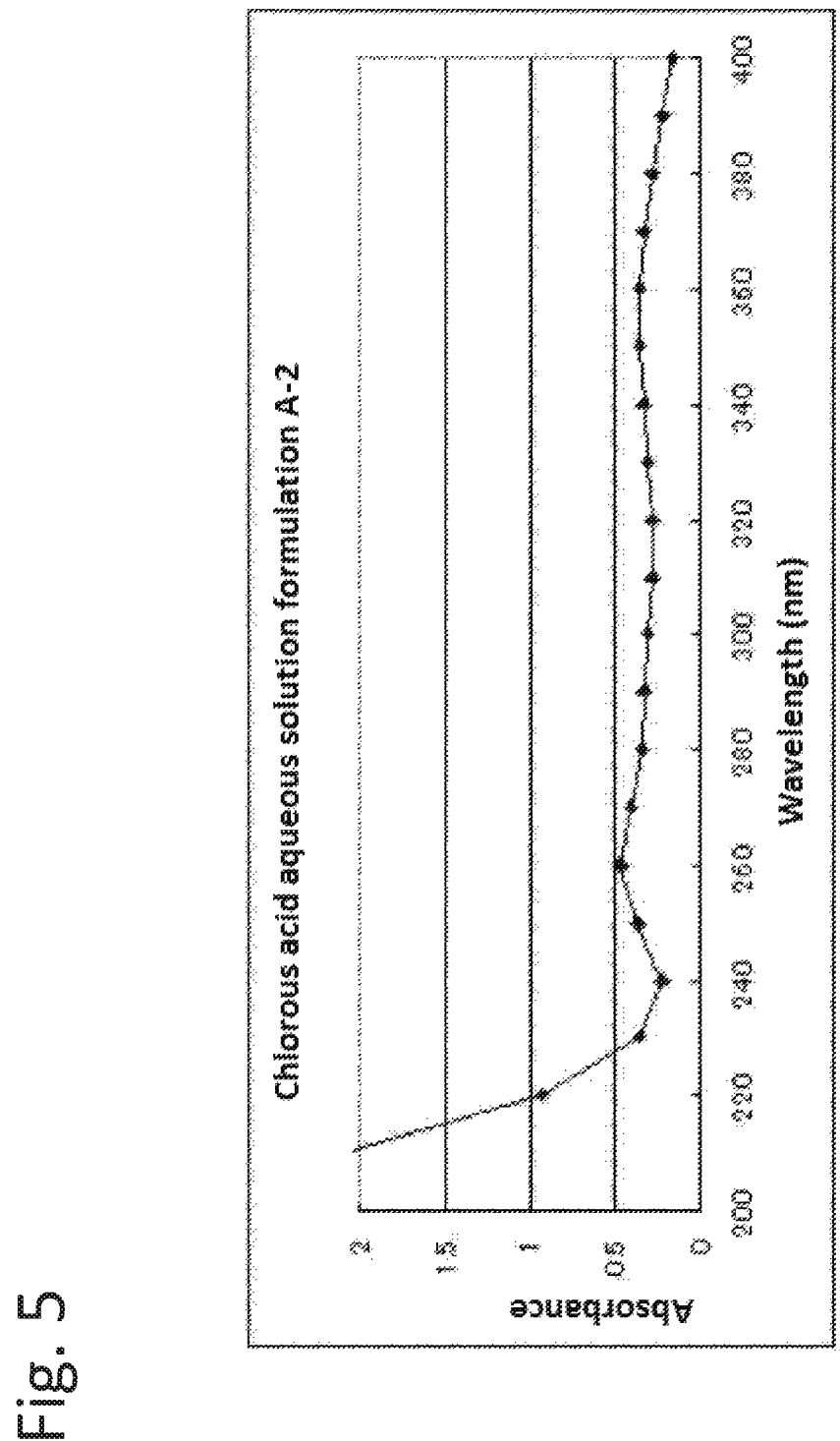
FIG. 5 shows the UV spectrum in Example 4. A double peak is observed.

The UV spectrum is shown in FIG. 5. The UV spectrum, as shown, has a double peak, confirming that a chlorous acid aqueous solution with a sterilizing effect retained is correctly manufactured.

Example 5: Manufacturing Example 3 of Chlorous Acid Aqueous Solution (CAAS A-3)

In Example 5, a chlorous acid aqueous solution was manufactured according to the following procedure based on the conditions for CAAS A-3 in (Production condition of chlorous acid aqueous solution).

(Method)
(1) Table of blended ingredient d was loaded into 2.
(2) Table of blended ingredient c was loaded into 1. The pH of the aqueous solution A was 11.0.
(3) A tank containing 0.9%±0.1% chlorine dioxide gas was prepared for 3.
(4) 4 was put into operation.
(5) 5 was released open to allow chlorine dioxide gas to flow into 1 at a flow rate of 210 ppm/minute (210 ppm/min±40 ppm/min (660 mg·ClO₂/min to 530 mg·ClO₂/min)).
(6) 5 was closed after the gas had flowed in for 15 minutes.
(7) 4 was stopped.
(8) The mixture was left standing for 15 minutes.
(9) 4 was again put into operation, and (4)-(8) were repeated 1 to 2 times (actual total time of chlorine dioxide gas flowing in was 15 to 30 minutes).
(10) The liquid in 1 was considered a chlorous acid aqueous solution.

The test results for the manufactured product are shown below.

TABLE 12

Chlorous acid aqueous solution A-3

| Tested item | Specification | Result |
|---|---|---|
| Potassium permanganate | When potassium permanganate solution (1→300) is added to 5 ml of the present product (1→20), the mixture turns reddish purple. When 1 ml of sulfuric acid (1→20) | When potassium permanganate solution (1→300) was added to 5 ml of the present product (1→20), the mixture turned reddish purple. When 1 ml of sulfuric acid (1→20) |

TABLE 12-continued

Chlorous acid aqueous solution A-3

| Tested item | Specification | Result |
|---|---|---|
| | acid (1→20) is added thereto, the mixture turns light yellow. | was added thereto, the mixture turned light yellow. |
| UV spectrum | An aqueous solution of the present product has maximum absorbance sections at wavelengths 258 to 262 nm and 346 to 361 nm. | An aqueous solution of the present product had maximum absorbance sections at wavelengths 258 to 262 nm and 346 to 361 nm. |
| Potassium iodide starch paper | When potassium iodide starch paper is immersed in the present product, the potassium iodide starch paper changes to a blue color and then the color fades. | When potassium iodide starch paper was immersed in the present product, the potassium iodide starch paper changed to a blue color and then the color faded. |
| Chlorous acid concentration | . . . | 13000 ppm |

Figure 6:
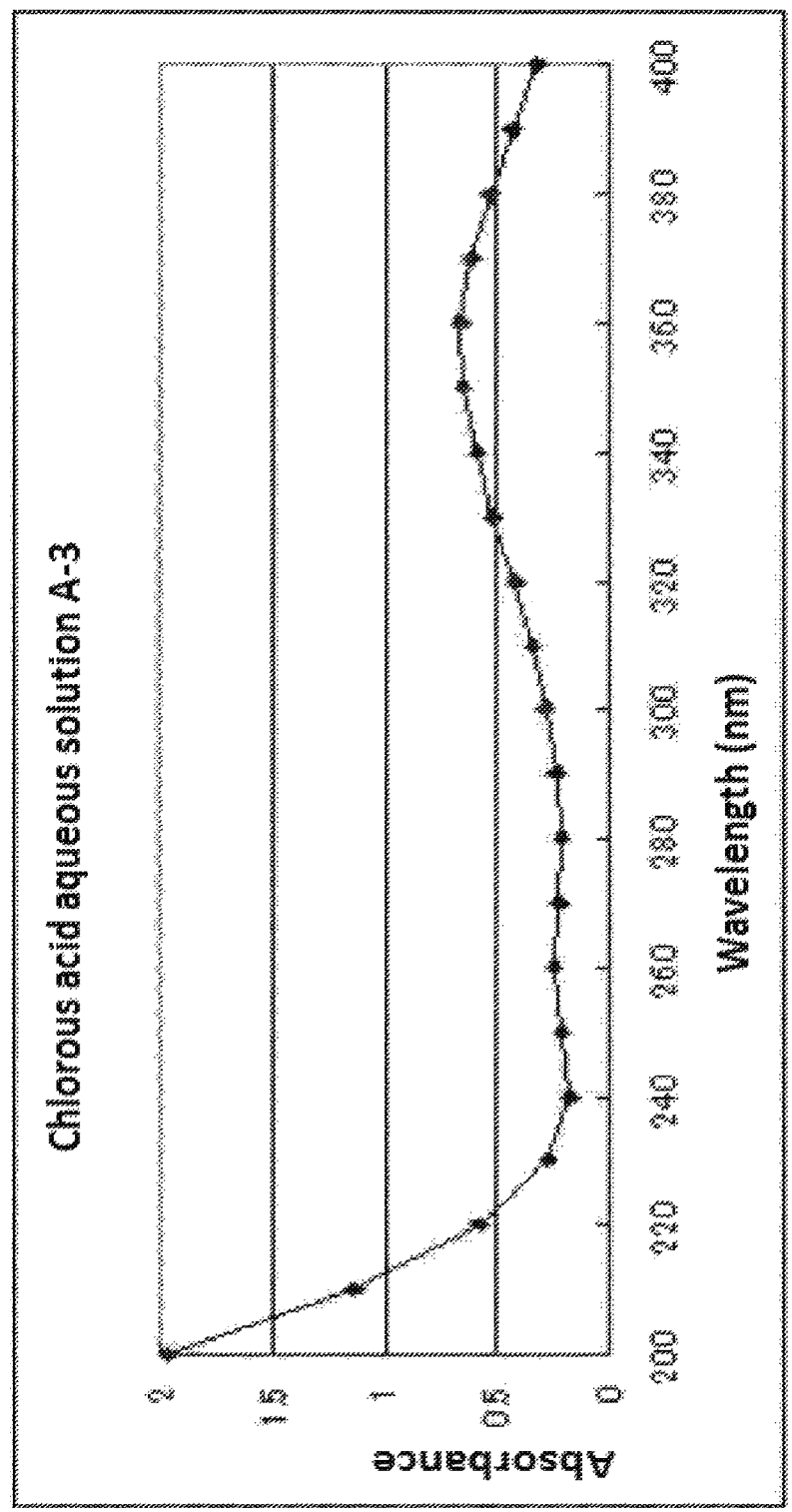
FIG. 6 shows the UV spectrum in Example 5. A double peak is observed.

The UV spectrum is shown in FIG. 6. The UV spectrum, as shown, has a double peak, confirming that a chlorous acid aqueous solution with a sterilizing effect retained is correctly manufactured.

Example 6: Manufacturing Example 3 of Chlorous Acid Aqueous Solution Formulation (CAAS A-3)

In Example 6, a chlorous acid aqueous solution formulation was manufactured according to the following procedure by using CAAS A-3 in Example 5.

Aqueous solution B was made based on the following.

TABLE 13

| Raw material | Blend ratio |
|---|---|
| Chlorous acid aqueous solution A-3 | 75.0% |
| Potassium dihydrogenphosphate | 1.4% |
| Potassium hydroxide | 0.6% |
| Purified water | 23.0% |
| Total | 100.0% |

The pH at this time was 6.8.
The test results for the manufactured product are shown below.

TABLE 14

Chlorous acid aqueous solution formulation A-3

| Tested item | Specification | Result |
|---|---|---|
| Potassium permanganate | When potassium permanganate solution (1→300) is added to 5 ml of the present product (1→20), the mixture turns reddish purple. When 1 ml of sulfuric acid (1→20) is added thereto, the mixture turns light yellow. | When potassium permanganate solution (1→300) was added to 5 ml of the present product (1→20), the mixture turned reddish purple. When 1 ml of sulfuric acid (1→20) was added thereto, the mixture turned light yellow. |
| UV spectrum | An aqueous solution of the present product has maximum absorbance sections at | An aqueous solution of the present product had maximum absorbance sections at |

TABLE 14-continued

Chlorous acid aqueous solution formulation A-3

| Tested item | Specification | Result |
|---|---|---|
| | at wavelengths 258 to 262 nm and 346 to 361 nm. | wavelengths 258 to 262 nm and 346 to 361 nm. |
| Potassium iodide starch paper | When potassium iodide starch paper is immersed in the present product, the potassium iodide starch paper changes to a blue color and then the color fades. | When potassium iodide starch paper was immersed in the present product, the potassium iodide starch paper changed to a blue color and then the color faded. |
| Chlorous acid concentration | . . . | 10000 ppm |

Figure 7:
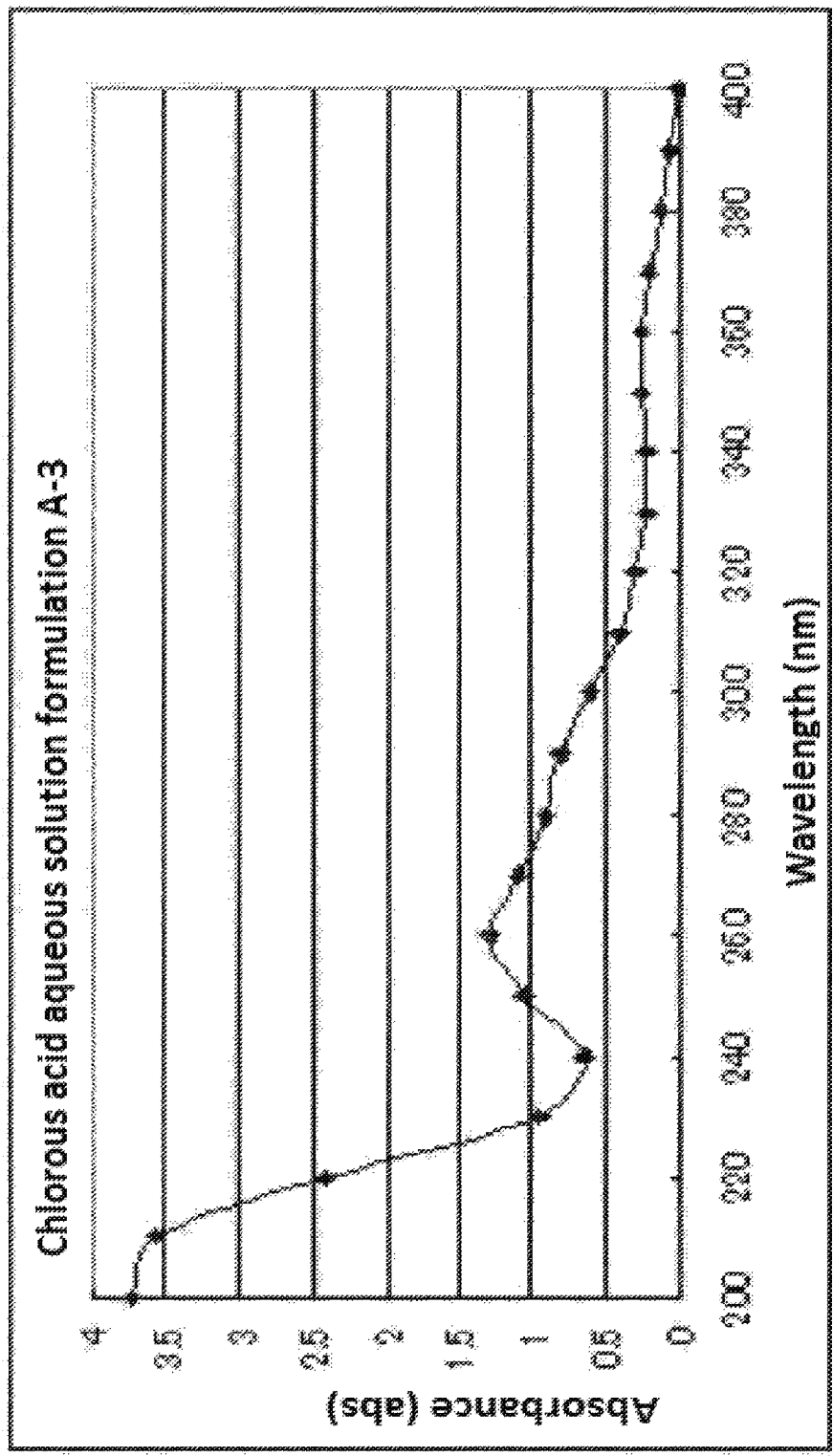
FIG. 7 shows the UV spectrum in Example 6. A double peak is observed.

The UV spectrum is shown in FIG. 7. The UV spectrum, as shown, has a double peak, confirming that a chlorous acid aqueous solution with a sterilizing effect retained is correctly manufactured.

Example 7: Sterilization Power Test/Stability Test

The following experiment was conducted to examine the effects of CAAS formulations A-1 to A-2 manufactured in Examples 2 and 4.

For stability, a compound (called "ASC" herein) in which 1N hydrochloric acid was added to 6% sodium chlorite to adjust the pH to 2.3 to 2.9 was used as a control. ASC, together with 2 types of chlorous acid aqueous solution manufactured in Examples 2 and 4, was sealed and stored at 4° C. in a dark room to examine the stability.

In the test to examine the sterilization effect, a change over time in sterilization effects immediately after manufacture, on day 5, and day 10 was examined. The sterilization effect on *E. coli* was assessed by a carbolic acid coefficient.

To examine the chlorous acid concentration, iodometric titration was performed on ASC and the 2 types of chlorous acid aqueous solution manufactured in Examples 2 and 4 on day 1, day 5, and day 10 to find the chlorous acid concentration.

The results thereof are shown below.

TABLE 15-1

Sterilization effect examination table
(ASC) Immediately after manufacture

| Carbolic acid concentration | | Contact time | | | |
|---|---|---|---|---|---|
| % | ppm | 1 min. | 5 min. | 10 min. | 15 min. |
| 2.070% | 20000 ppm | − | − | − | − |
| 1.500% | 15000 ppm | + | − | − | − |
| 1.000% | 10000 ppm | + | + | − | − |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |

| Chlorous acid concentration | | Contact time | | | |
|---|---|---|---|---|---|
| % | ppm | 1 min. | 5 min. | 10 min. | 15 min. |
| 0.015% | 150 ppm | − | − | − | − |
| 0.010% | 100 ppm | − | − | − | − |
| 0.008% | 80 ppm | − | − | − | − |
| 0.007% | 70 ppm | − | − | − | − |
| 0.006% | 60 ppm | − | − | − | − |

TABLE 15-1-continued

Sterilization effect examination table (ASC) Immediately after manufacture

| % | ppm | 1 min. | 5 min. | 10 min. | 15 min. |
|---|---|---|---|---|---|
| 0.005% | 50 ppm | + | − | − | − |
| 0.004% | 40 ppm | + | − | − | − |
| 0.003% | 30 ppm | + | + | + | − |
| 0.002% | 20 ppm | + | + | + | + |
| 0.001% | 10 ppm | + | + | + | + |
| 0.000% | 0 ppm | + | + | + | + |

TABLE 15-2

Sterilization effect examination table (ASC) Day 5

| Carbolic acid concentration | | Contact time | | | |
|---|---|---|---|---|---|
| % | ppm | 1 min. | 5 min. | 10 min. | 15 min. |
| 2.070% | 20000 ppm | − | − | − | − |
| 1.500% | 15000 ppm | + | − | − | − |
| 1.000% | 10000 ppm | + | + | − | − |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |

| Chlorous acid concentration | | Contact time | | | |
|---|---|---|---|---|---|
| % | ppm | 1 min. | 5 min. | 10 min. | 15 min. |
| 2.070% | 20000 ppm | + | + | + | + |
| 1.500% | 15000 ppm | + | + | + | + |
| 1.000% | 10000 ppm | + | + | + | + |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |
| 0.005% | 50 ppm | + | + | + | + |
| 0.001% | 10 ppm | + | + | + | + |
| 0.000% | 0 ppm | + | + | + | + |

TABLE 15-3

Sterilization effect examination table (ASC) Day 10

| Carbolic acid concentration | | Contact time | | | |
|---|---|---|---|---|---|
| % | ppm | 1 min. | 5 min. | 10 min. | 15 min. |
| 2.070% | 20000 ppm | − | − | − | − |
| 1.500% | 15000 ppm | + | − | − | − |
| 1.000% | 10000 ppm | + | + | − | − |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |

| Chlorous acid concentration | | Contact time | | | |
|---|---|---|---|---|---|
| % | ppm | 1 min. | 5 min. | 10 min. | 15 min. |
| 2.070% | 20000 ppm | + | + | + | + |
| 1.500% | 15000 ppm | + | + | + | + |
| 1.000% | 10000 ppm | + | + | + | + |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |
| 0.005% | 50 ppm | + | + | + | + |
| 0.001% | 10 ppm | + | + | + | + |
| 0.000% | 0 ppm | + | + | + | + |

TABLE 16-1

Sterilization effect examination table (A-1) Immediately after manufacture

| Carbolic acid concentration | | Contact time | | | |
|---|---|---|---|---|---|
| % | ppm | 1 min. | 5 min. | 10 min. | 15 min. |
| 2.070% | 20000 ppm | − | − | − | − |
| 1.500% | 15000 ppm | + | − | − | − |
| 1.000% | 10000 ppm | + | + | − | − |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |

| Chlorous acid concentration | | Contact time | | | |
|---|---|---|---|---|---|
| % | ppm | 1 min. | 5 min. | 10 min. | 15 min. |
| 0.015% | 150 ppm | − | − | − | − |
| 0.010% | 100 ppm | − | − | − | − |
| 0.008% | 80 ppm | − | − | − | − |
| 0.007% | 70 ppm | − | − | − | − |
| 0.006% | 60 ppm | − | − | − | − |
| 0.005% | 50 ppm | − | − | − | − |
| 0.004% | 40 ppm | + | + | − | − |
| 0.003% | 30 ppm | + | + | + | + |
| 0.002% | 20 ppm | + | + | + | + |
| 0.001% | 10 ppm | + | + | + | + |
| 0.000% | 0 ppm | + | + | + | + |

TABLE 16-2

Sterilization effect examination table (A-1) Day 5

| Carbolic acid concentration | | Contact time | | | |
|---|---|---|---|---|---|
| % | ppm | 1 min. | 5 min. | 10 min. | 15 min. |
| 2.070% | 20000 ppm | − | − | − | − |
| 1.500% | 15000 ppm | + | − | − | − |
| 1.000% | 10000 ppm | + | + | − | − |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |

| Chlorous acid concentration | | Contact time | | | |
|---|---|---|---|---|---|
| % | ppm | 1 min. | 5 min. | 10 min. | 15 min. |
| 0.015% | 150 ppm | − | − | − | − |
| 0.010% | 100 ppm | − | − | − | − |
| 0.008% | 80 ppm | − | − | − | − |
| 0.007% | 70 ppm | − | − | − | − |
| 0.006% | 60 ppm | − | − | − | − |
| 0.005% | 50 ppm | − | − | − | − |
| 0.004% | 40 ppm | + | + | − | − |
| 0.003% | 30 ppm | + | + | + | − |
| 0.002% | 20 ppm | + | + | + | + |

TABLE 16-2-continued

Sterilization effect examination table (A-1) Day 5

| 0.001% | 10 ppm | + | + | + | + |
|---|---|---|---|---|---|
| 0.000% | 0 ppm | + | + | + | + |

TABLE 16-3

Sterilization effect examination table (A-1) Day 10

| Carbolic acid concentration | | Contact time | | | |
|---|---|---|---|---|---|
| % | ppm | 1 min. | 5 min. | 10 min. | 15 min. |
| 2.070% | 20000 ppm | − | − | − | − |
| 1.500% | 15000 ppm | + | − | − | − |
| 1.000% | 10000 ppm | + | + | − | − |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |

| Chlorous acid concentration | | Contact time | | | |
|---|---|---|---|---|---|
| % | ppm | 1 min. | 5 min. | 10 min. | 15 min. |
| 0.015% | 150 ppm | − | − | − | − |
| 0.010% | 100 ppm | − | − | − | − |
| 0.008% | 80 ppm | − | − | − | − |
| 0.007% | 70 ppm | − | − | − | − |
| 0.006% | 60 ppm | − | − | − | − |
| 0.005% | 50 ppm | − | − | − | − |
| 0.004% | 40 ppm | + | + | − | − |
| 0.003% | 30 ppm | + | + | + | + |
| 0.002% | 20 ppm | + | + | + | + |
| 0.001% | 10 ppm | + | + | + | + |
| 0.000% | 0 ppm | + | + | + | + |

TABLE 17-1

Sterilization effect examination table (A-2) Immediately after manufacture

| Carbolic acid concentration | | Contact time | | | |
|---|---|---|---|---|---|
| % | ppm | 1 min. | 5 min. | 10 min. | 15 min. |
| 2.070% | 20000 ppm | − | − | − | − |
| 1.500% | 15000 ppm | + | − | − | − |
| 1.000% | 10000 ppm | + | + | − | − |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |

| Chlorous acid concentration | | Contact time | | | |
|---|---|---|---|---|---|
| % | ppm | 1 min. | 5 min. | 10 min. | 15 min. |
| 0.015% | 150 ppm | − | − | − | − |
| 0.010% | 100 ppm | − | − | − | − |
| 0.008% | 80 ppm | − | − | − | − |
| 0.007% | 70 ppm | − | − | − | − |
| 0.006% | 60 ppm | − | − | − | − |
| 0.005% | 50 ppm | − | − | − | − |
| 0.004% | 40 ppm | − | − | − | − |
| 0.003% | 30 ppm | + | + | − | − |
| 0.002% | 20 ppm | + | + | + | + |
| 0.001% | 10 ppm | + | + | + | + |
| 0.000% | 0 ppm | + | + | + | + |

TABLE 17-2

Sterilization effect examination table (A-2) Day 5

| Carbolic acid concentration | | Contact time | | | |
|---|---|---|---|---|---|
| % | ppm | 1 min. | 5 min. | 10 min. | 15 min. |
| 2.070% | 20000 ppm | − | − | − | − |
| 1.500% | 15000 ppm | + | − | − | − |
| 1.000% | 10000 ppm | + | + | − | − |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |

| Chlorous acid concentration | | Contact time | | | |
|---|---|---|---|---|---|
| % | ppm | 1 min. | 5 min. | 10 min. | 15 min. |
| 0.015% | 150 ppm | − | − | − | − |
| 0.010% | 100 ppm | − | − | − | − |
| 0.008% | 80 ppm | − | − | − | − |
| 0.007% | 70 ppm | − | − | − | − |
| 0.006% | 60 ppm | − | − | − | − |
| 0.005% | 50 ppm | − | − | − | − |
| 0.004% | 40 ppm | − | − | − | − |
| 0.003% | 30 ppm | + | + | − | − |
| 0.002% | 20 ppm | + | + | + | + |
| 0.001% | 10 ppm | + | + | + | + |
| 0.000% | 0 ppm | + | + | + | + |

TABLE 17-3

Sterilization effect examination table (A-2) Day 10

| Carbolic acid concentration | | Contact time | | | |
|---|---|---|---|---|---|
| % | ppm | 1 min. | 15 min. | 10 min. | 15 min. |
| 2.070% | 20000 ppm | − | − | − | − |
| 1.500% | 15000 ppm | + | − | − | − |
| 1.000% | 10000 ppm | + | + | − | − |
| 0.700% | 7000 ppm | + | + | + | + |
| 0.500% | 5000 ppm | + | + | + | + |
| 0.300% | 3000 ppm | + | + | + | + |
| 0.100% | 1000 ppm | + | + | + | + |
| 0.010% | 100 ppm | + | + | + | + |

| Chlorous acid concentration | | Contact time | | | |
|---|---|---|---|---|---|
| % | ppm | 1 min. | 5 min. | 10 min. | 5 min. |
| 0.015% | 150 ppm | − | − | − | − |
| 0.010% | 100 ppm | − | − | − | − |
| 0.008% | 80 ppm | − | − | − | − |
| 0.007% | 70 ppm | − | − | − | − |
| 0.006% | 60 ppm | − | − | − | − |
| 0.005% | 50 ppm | − | − | − | − |
| 0.004% | 40 ppm | − | − | − | − |
| 0.003% | 30 ppm | + | + | − | − |
| 0.002% | 20 ppm | + | + | + | + |
| 0.001% | 10 ppm | + | + | + | + |
| 0.000% | 0 ppm | + | + | + | + |

The advantage in using gaseous chlorine dioxide (gas) includes the following: a transitional state is created and a decomposition reaction is delayed such that chlorous acid ($HClO_2$) can be stably maintained over a long period of time.

Figure 8:
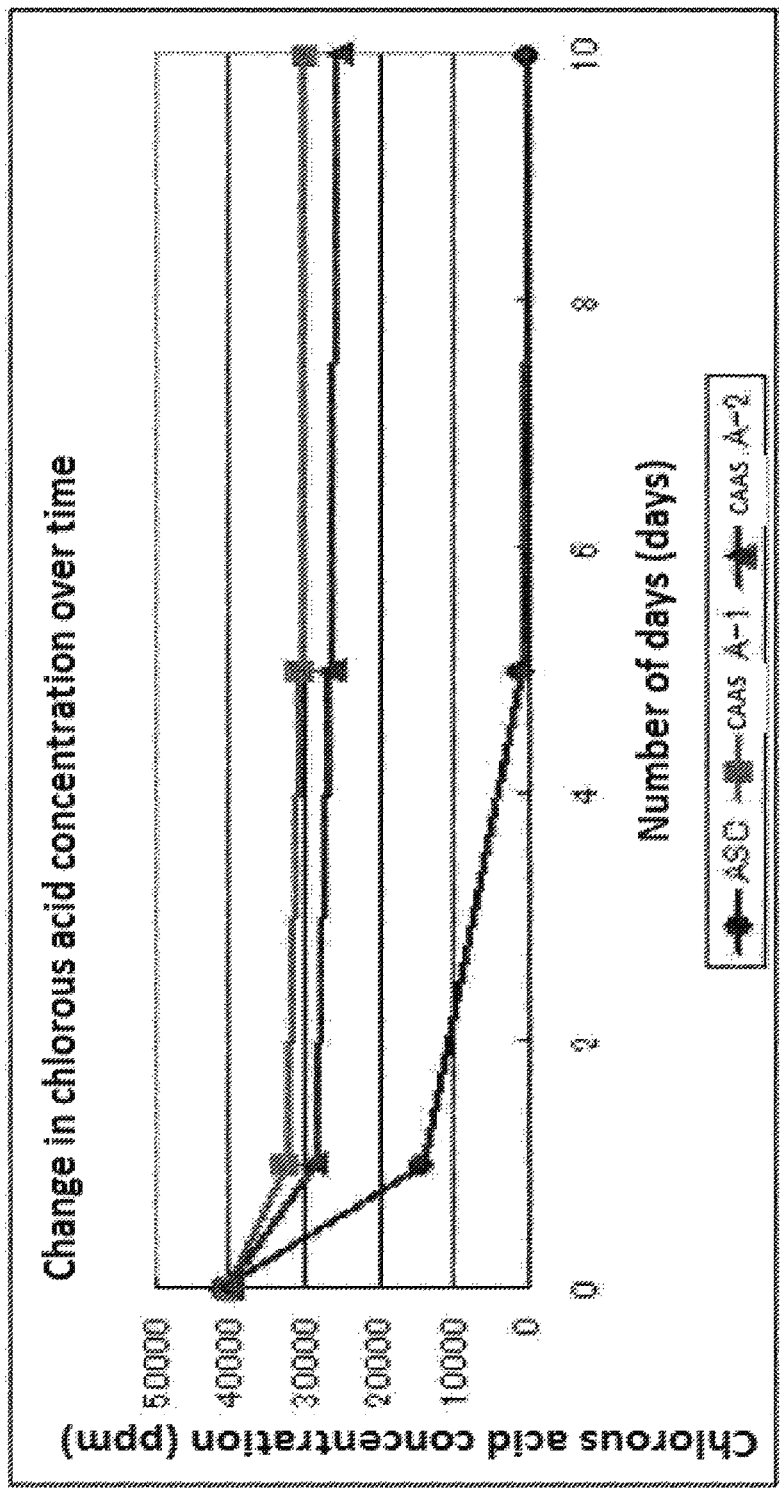
FIG. 8 shows the stability of the chlorous acid aqueous solutions manufactured in Examples 2 and 4 compared to the control, which was conducted in Example 7. The horizontal axis indicates the number of days, and the vertical axis indicates the chlorous acid concentration.

FIG. 8 shows a graph of results summarizing the above.
As shown in Tables 15-1 to 15-3 and FIG. 8, the chlorous acid aqueous solution concentration in the control, ASC, has nearly disappeared on day 5, and the sterilization effect on *E. coli* has also disappeared. Meanwhile, as shown in Tables 16-1 to 16-3, 17-1 to 17-3 and FIG. 8, the chlorous acid aqueous solution concentration of chlorous acid aqueous solution formulation A-1 and chlorous acid aqueous solution formulation A-2 dramatically decreased immediately after manufacture, but stabilized thereafter despite with a gradual decrease. The sterilization effect on *E. coli* was also maintained. Since there is hardly any difference in the sterilization effect when data for immediately after manufacture and day 10 are compared, it is understood as a manufacturing method of a chlorous acid aqueous solution which can stably exhibit a sterilizing effect for at least 10 days. Although not wishing to be bound by any theory, this has demonstrated that a chlorous acid aqueous solution manufactured by the manufacturing method of the present invention creates a transitional state and delays a decomposition reaction such that chlorous acid ($HClO_2$) is stably maintained in an aqueous solution over a long period of time.

As described above, the present invention is exemplified by the use of its preferred Embodiments and Examples. However, the present invention is not limited thereto. Various embodiments can be practiced within the scope of the structures recited in the claims. It is understood that the scope of the present invention should be interpreted solely based on the claims. Furthermore, it is understood that any patent, any patent application, and references cited herein should be incorporated herein by reference in the same manner as the content are specifically described herein.

INDUSTRIAL APPLICABILITY

An aqueous solution comprising a chlorous acid aqueous solution obtained by the present invention can be utilized in applications such as sterilizing agents as well as deodorants, bleaching agents, blood stain removing agents, and the like.

The invention claimed is:

1. A method of manufacturing a chlorous acid aqueous solution, comprising the step of:
generating chlorous acid by trapping chlorine dioxide ($ClO_2$) with aqueous solution A comprising hydrogen peroxide and one of an inorganic acid, inorganic acid salt, organic acid, and organic acid salt, two or more types thereof or a combination thereof,
wherein the chlorine dioxide ($ClO_2$) is provided as gas and a pH of the aqueous solution A prior to addition of the chlorine dioxide ($ClO_2$) is 11.0 or less and greater than 7.0,
wherein TAL of the aqueous solution A is 20 to 2000, and wherein the TAL is found by an amount of 0.1N—HCl titration from an initial pH at or below pH of 11.0 to a pH of 4; and
after the step of trapping, a step of further adding aqueous solution B comprising one of an inorganic acid, inorganic acid salt, organic acid, and organic acid salt, two or more types thereof or a combination thereof,
wherein a pH of a liquid after adding the aqueous solution B is 3.2 or greater and less than 7.0.

2. The method of claim 1, wherein a pH of the aqueous solution A is 10.8 or less and 10.2 or greater.

3. The method of claim 1, wherein the inorganic acid is carbonic acid, phosphoric acid, boric acid, or sulfuric acid.

4. The method of claim 1, wherein the inorganic acid salt is carbonate, hydroxide, phosphate, or borate.

5. The method of claim 4, wherein the carbonate is sodium carbonate, potassium carbonate, sodium bicarbonate, or potassium bicarbonate.

6. The method of claim 4, wherein the hydroxide is sodium hydroxide, potassium hydroxide, calcium hydroxide, or barium hydroxide.

7. The method of claim 4, wherein the phosphate is disodium hydrogen phosphate, sodium dihydrogen phosphate, trisodium phosphate, tripotassium phosphate, dipotassium hydrogen phosphate, or potassium dihydrogen phosphate.

8. The method of claim 4, wherein the borate is sodium borate or potassium borate.

9. The method of claim 1, wherein the organic acid is succinic acid, citric acid, malic acid, acetic acid, or lactic acid.

10. The method of claim 1, wherein the organic acid salt is sodium succinate, potassium succinate, sodium citrate, potassium citrate, sodium malate, potassium malate, sodium acetate, potassium acetate, sodium lactate, potassium lactate, or calcium lactate.

11. The method of claim 1, wherein a pH of a liquid after adding the aqueous solution B is 4.0 or greater and less than 7.0.

12. The method of claim 1, wherein a pH of a liquid after adding the aqueous solution B is about 5.0 or greater and less than 7.0.

13. The method of claim 1, wherein the chlorine dioxide is present at a concentration of 0.8 to 1.0%.

14. A chlorous acid aqueous solution manufactured by a method comprising the step of trapping chlorine dioxide ($ClO_2$) with aqueous solution A comprising hydrogen peroxide and one of an inorganic acid, inorganic acid salt, organic acid, and organic acid salt, two or more types thereof or a combination thereof, the chlorine dioxide ($ClO_2$) being provided as gas and a pH of the aqueous solution A prior to addition of the chlorine dioxide ($ClO_2$) being 11.0 or less and greater than 7.0 wherein TAL of the aqueous solution A is 20 to 2000, and wherein the TAL is found by an amount of 0.1N—HCl titration from an initial pH at or below pH of 11.0 to a pH of 4; and after the step of trapping, a step of further adding aqueous solution B comprising one of an inorganic acid, inorganic acid salt, organic acid, and organic acid salt, two or more types thereof or a combination thereof, a pH of a liquid after adding the aqueous solution B being 3.2 or greater and less than 7.0.

15. The chlorous acid aqueous solution of claim 14, wherein a pH of the aqueous solution A is 10.8 or less and 10.2 or greater.

* * * * *